(12) United States Patent
Yomtov et al.

(10) Patent No.: US 11,458,320 B2
(45) Date of Patent: *Oct. 4, 2022

(54) METHOD OF CARDIAC RESYNCHRONIZATION THERAPY

(71) Applicant: PEACS INVESTMENTS B.V., Nieuwerbrug aan den Rijn (NL)

(72) Inventors: Barry Yomtov, Marblehead, MA (US); Robert Pacheco, Bayside, NY (US)

(73) Assignee: PEACS INVESTMENTS B.V., Nieuwerbrug aan den Rijn (NL)

( * ) Notice: Subject to any disclaimer, the term of this patent is extended or adjusted under 35 U.S.C. 154(b) by 358 days.

This patent is subject to a terminal disclaimer.

(21) Appl. No.: 16/670,672

(22) Filed: Oct. 31, 2019

(65) Prior Publication Data
US 2020/0061383 A1 Feb. 27, 2020

Related U.S. Application Data

(63) Continuation-in-part of application No. 15/695,332, filed on Sep. 5, 2017, now Pat. No. 10,471,263.
(Continued)

(51) Int. Cl.
*A61N 1/372* (2006.01)
*A61N 1/368* (2006.01)
*A61N 1/375* (2006.01)

(52) U.S. Cl.
CPC ....... *A61N 1/36843* (2017.08); *A61N 1/3682* (2013.01); *A61N 1/3756* (2013.01); *A61N 1/37205* (2013.01)

(58) Field of Classification Search
CPC .... A61N 1/37247; A61B 5/04; A61B 5/0402; A61B 5/4836
See application file for complete search history.

(56) References Cited

U.S. PATENT DOCUMENTS

| 5,657,755 A | 8/1997 | Desai |
| 6,575,659 B1 | 6/2003 | Valtwies et al. |
| (Continued) | | |

FOREIGN PATENT DOCUMENTS

| CN | 1901836 A | 1/2007 |
| CN | 101828915 A | 9/2010 |
| (Continued) | | |

OTHER PUBLICATIONS

International Bureau, International Preliminary Report on Patentability dated Mar. 21, 2019 for International Application No. PCT/US2017/050188, 9 pages.
(Continued)

*Primary Examiner* — Joseph M Dietrich
(74) *Attorney, Agent, or Firm* — Foley & Lardner LLP

(57) ABSTRACT

Various embodiments include methods of cardiac resynchronization therapy (CRT). Various embodiments may include: generating, using a processing unit, a cardiac activation map including a three-dimensional (3D) heart model of the heart that shows coronary vessels of a patient and shows the propagation of electrical signals through the 3D heart model; determining the location of a left bundle branch block (LBBB) based on the cardiac activation map; implanting a first pacing device and a second pacing device into the patient; stimulating the His Bundle of the heart using the first pacing device; and stimulating the left ventricle (LV) of the heart at a position downstream of the LBBB with respect to a direction of electrical conduction through the LV using the second pacing device after stimulating the His bundle.

15 Claims, 13 Drawing Sheets

Related U.S. Application Data

(60) Provisional application No. 62/888,496, filed on Aug. 18, 2019, provisional application No. 62/383,804, filed on Sep. 6, 2016.

(56) References Cited

U.S. PATENT DOCUMENTS

| | | |
|---|---|---|
| 6,575,969 B1 | 6/2003 | Rittman et al. |
| 7,155,042 B1 | 12/2006 | Cowan et al. |
| 7,382,907 B2 | 6/2008 | Luo et al. |
| 7,787,951 B1 | 8/2010 | Min |
| 7,860,558 B2 | 12/2010 | Feild et al. |
| 8,155,739 B2 | 4/2012 | Keel et al. |
| 8,326,419 B2 | 12/2012 | Rosenberg et al. |
| 8,478,388 B2 | 7/2013 | Nguyen et al. |
| 8,615,298 B2 | 12/2013 | Ghosh et al. |
| 9,078,573 B2 | 7/2015 | Ramanathan et al. |
| 9,155,897 B2 | 10/2015 | Ghosh et al. |
| 9,265,951 B2 | 2/2016 | Sweeney |
| 9,278,219 B2 | 3/2016 | Ghosh |
| 9,381,363 B2 | 7/2016 | Ryu et al. |
| 9,439,578 B2 | 9/2016 | Thakur et al. |
| 9,510,763 B2 | 12/2016 | Ghosh et al. |
| 9,579,064 B2 | 2/2017 | Kovtun et al. |
| 9,586,052 B2 | 3/2017 | Gillberg et al. |
| 9,681,817 B2 | 6/2017 | Maskara et al. |
| 9,875,544 B2 | 1/2018 | Rai et al. |
| 9,877,789 B2 | 1/2018 | Ghosh |
| 9,986,928 B2 | 6/2018 | Gillberg et al. |
| 10,016,145 B2 | 7/2018 | Thakur et al. |
| 10,369,358 B2 | 8/2019 | Monteiro |
| 10,471,263 B2 | 11/2019 | Pacheco |
| 10,713,790 B2 | 7/2020 | Adler |
| 10,932,863 B2 | 3/2021 | Adler |
| 2002/0105516 A1 | 8/2002 | Tracy |
| 2002/0128565 A1 | 9/2002 | Rudy |
| 2005/0096515 A1 | 5/2005 | Geng |
| 2005/0096522 A1 | 5/2005 | Reddy et al. |
| 2006/0079759 A1 | 4/2006 | Vaillant et al. |
| 2006/0224071 A1 | 10/2006 | Stewart |
| 2007/0270703 A1 | 11/2007 | He et al. |
| 2008/0205716 A1 | 8/2008 | Derg et al. |
| 2009/0088655 A1 | 4/2009 | Vajdic et al. |
| 2009/0099619 A1 | 4/2009 | Lessmeier et al. |
| 2009/0099679 A1 | 4/2009 | Sandoval et al. |
| 2009/0287087 A1 | 11/2009 | Gwerder et al. |
| 2010/0070249 A1 | 3/2010 | Ionasec et al. |
| 2010/0160773 A1 | 6/2010 | Cohen et al. |
| 2010/0268059 A1 | 10/2010 | Ryu et al. |
| 2010/0280399 A1 | 11/2010 | Francis et al. |
| 2010/0312100 A1 | 12/2010 | Zarkh et al. |
| 2011/0060576 A1 | 3/2011 | Sharma et al. |
| 2011/0071583 A1 | 3/2011 | Muntendam |
| 2012/0061612 A1 | 3/2012 | Yoshioka et al. |
| 2012/0157822 A1 | 6/2012 | Van Dam et al. |
| 2012/0230565 A1 | 9/2012 | Steinberg et al. |
| 2012/0235993 A1 | 9/2012 | Kim |
| 2012/0283587 A1 | 11/2012 | Gosh et al. |
| 2013/0060315 A1 | 3/2013 | Elghazzawi et al. |
| 2013/0116533 A1 | 5/2013 | Lian et al. |
| 2013/0177223 A1 | 7/2013 | Lee et al. |
| 2013/0184697 A1 | 7/2013 | Han et al. |
| 2013/0197881 A1 | 8/2013 | Mansi et al. |
| 2013/0245473 A1 | 9/2013 | Ramanathan et al. |
| 2013/0304407 A1 | 11/2013 | George et al. |
| 2014/0088943 A1 | 3/2014 | Trayanova et al. |
| 2014/0107510 A1 | 4/2014 | Begun et al. |
| 2014/0121636 A1 | 5/2014 | Boyden et al. |
| 2014/0194760 A1 | 7/2014 | Albert |
| 2014/0207005 A1 | 7/2014 | Bukkapatnam et al. |
| 2014/0371807 A1 | 12/2014 | Ghosh et al. |
| 2015/0170978 A1 | 6/2015 | Chen et al. |
| 2015/0294082 A1 | 10/2015 | Passerini et al. |
| 2015/0356742 A1 | 12/2015 | Barbarito et al. |
| 2016/0331261 A1 | 11/2016 | Someya et al. |
| 2016/0342761 A1 | 11/2016 | Whiting et al. |
| 2016/0345833 A1 | 12/2016 | Adams |
| 2017/0011197 A1 | 1/2017 | Van Dam et al. |
| 2017/0071492 A1 | 3/2017 | van Dam et al. |
| 2017/0071675 A1 | 3/2017 | Dawoud et al. |
| 2017/0178403 A1 | 6/2017 | Krummen et al. |
| 2017/0209698 A1 | 7/2017 | Villongco et al. |
| 2018/0064947 A1 | 3/2018 | Pacheco et al. |
| 2018/0303345 A1 | 10/2018 | Adler |
| 2019/0038357 A1 | 2/2019 | Adler |
| 2019/0111265 A1 | 4/2019 | Zhou |
| 2020/0029817 A1 | 1/2020 | Adler |
| 2020/0061383 A1 | 2/2020 | Yomtov et al. |

FOREIGN PATENT DOCUMENTS

| | | |
|---|---|---|
| EP | 2 675 354 A4 | 12/2013 |
| WO | 2009/129475 | 10/2009 |
| WO | 2012061612 A2 | 5/2012 |
| WO | 2013006713 A2 | 1/2013 |
| WO | 2015170978 A1 | 11/2015 |

OTHER PUBLICATIONS

Daubert, et al., "Avoiding non-responders to cardiac resynchronization therapy: a practical guide", European Heart Journal Advance Access, European Heart Journal, doi:10.1093/eurheartj/ehw270, 13 pages, (Jul. 1, 2016).
Ploux, et al., "Noninvasive Electrocardiographic Mapping to Improve Patient Selection for Cardiac Resynchronization Therapy", Cardiac Resynchronization, Journal of the American College of Cardiology, vol. 61, No. 24, ISSN 00735-1097, 9 pages, (2013).
International Search Report and the Written Opinion of the International Searching Authority for International Application No. PCT/US2020/045764, dated Nov. 17, 2020, 13 pages.
Vijayaraman, Pugazhendhi et al., "His-optimized cardiac resynchronization therapy to maximize electrical resynchronization", Circulation: Arrhythmia and Electrophysiology, Feb. 2019, vol. 12, Article No. e006934, pp. 1-9.
Padeletti, Luigi et al., "Simultaneous his bundle and left ventricular pacing for optimal cardiac resynchronization therapy delivery", Circulation: Arrhythmia and Electrophysiology, 2016, vol. 9, Article No. e003793, pp. 1-8.
International Search Report and Written Opinion for counterpart Application No. PCT/US2019/043900, dated Nov. 20, 2019.
International Preliminary Report on Patentability for counterpart Application No. PCT/US2019/043900, dated Feb. 11, 2021.
International Search Report and Written Opinion for counterpart Application No. PCT/US2017/050188, dated Nov. 7, 2017.
International Search Report and Written Opinion for counterpart Application No. PCT/US2018/044746, dated Jan. 28, 2019.
International Preliminary Report on Patentability for counterpart Application No. PCT/US2018/044746, dated Feb. 13, 2020.
Invitation to Pay Additional Fees from EP for counterpart Application No. PCT/US2018/044746, dated Nov. 14, 2018.
Daubert, C., et al., "Avoiding non-re spenders to cardiac resynchronization therapy: a practical guide," European Heart Journal Advance Access, European Heart Journal, doi: 10.1093/eurheart/ehw270, published Jul. 1, 2016.
Ploux, Sylvain MD, et al., "Noninvasive Electrocardiographic Mapping to Improve Patient Selection for Cardiac Resynchronization Therapy," Journal of American College of Cardiology, vol. 61, No. 24, ISSN 0735-1097/$36.00, 2013, pp. 2435-2443.
Noheria, et al., "Ablating Premature Ventricular Complexes: Justification, Techniques, and Outcomes," MDCVJ | XI (2), houstonmethodist.org/debakey-journal, 2015, pp. 109-120.
Schulze, Walther et al., "Automatic camera-based identification and 3-D reconstruction of electrode positions in electrocardiographic imaging," Biomed. Eng.-Biomed. Tech. 59(6): 2014, pp. 515-528.
Van Dam, Peter, et al., "New Computer Program for detecting 12 Lead ECG Misplacement using a 3D Kinect Camera," Computing in Cardiology, 40, ISSN 2325-8861, 2013, pp. 1175-1178.

(56) References Cited

OTHER PUBLICATIONS

Vijayaraman, Pugazhendhi Dr., et al.. "His-Optimized Cardiac Resynchronization Therapy to Maximize Electrical Resynchronization A Feasibility Study," Circ Arrhythm Electrophysiol, Feb. 2019, 12:e006934. DOI: 10.1161/CIRCEP.118.006934, pp. 1-9.

Padeletti, Luigi MD., et al., "Simultaneous His Bundle and Left Ventricular Pacing for Optimal Cardiac Resynchronization Therapy Delivery Acute Hemodynamic Assessment by Pressure-Volume Loops," Circ Arrhythm Electrophysiol. 2016;9:e003793. DOI: 10.1161/CIRCEP.115.003793, pp. 1-8 (downloaded from http://ahajournals.org on Nov. 18, 2020).

Copending U.S. Appl. No. 17/174,308, Inventor: Barry Yomtov, Title: "Method of Providing Ventricular Arrythmia Localization and Myocardium Wall Thickness Within a 3D Heart Model," filed Feb. 11, 2021.

Copending U.S. Appl. No. 17/174,328, Inventor: Barry Yomtov, Title: "Method of Providing Ventricular Arrhythmia Localization with a Heart Model Derived from Machine Learning," filed Feb. 11, 2021.

"12 Lead ECG Placement example," YouTube video, published Feb. 18, 2015 [retrieved on 2018-20-23], Retrieved from the Internet:<URL:https://www.youtube.com/watch?v=0gAOy712-Gs>.

Mahmoud et al., "Interhospital Transfer Due to Failed Prehospital Diagnosis for Primary Percutaneous Coronary Intervention: an Observational Study on Incidence, Predictors, and Clinical Impact," European Heart Journal: Acute Cardiovascular Care 2(2), 2013, pp. 166-175.

Van Dam et al., "A New 3D Patient Specific Morphing Tool Enabling Clinical Application of Non-Invasive Cardiac Activation Imaging," 1 page.

Van Dam et al., "Non-Invasive Imaging of Cardiac Activation and Recovery," Annals of Biomedical Engineering, vol. 37, No. 9, Sep. 2009, pp. 1739-1756.

Wilson et al., "The Distribution of the Action Currents Produced by Heart Muscle and Other Excitable Tissues Immersed in Extensive Conducting Media," The Journal of General Physiology, Published Jan. 20, 1933, pp. 423-456.

"12 Lead ECG Placement example," YouTube video, published Feb. 18, 2015 [retrieved on 2018-20-23], Retrieved from the Internet:<URL:https://www.youtube.com/watch?v=0gAOy712-Gs>.

Fitzpatrick et al., "Handbook of Medical Imaging, vol. 2. Medical Image Processing and Analysis." Dec. 31, 2000, Chapter 8, pp. 449-445.

Franzone, Piero Colli, et al. "Spread of excitation in 3-D models of the anisotropic cardiac tissue. II. Effects of fiber architecture and ventricular geometry." Mathematical biosciences 147.2 (1998): 131-171.

Geselowitz, David B., "Description of Cardiac Sources in Anisotropic Cardiac Muscle: Application of Bidomain Model," Journal of Electrocardiology, vol. 25, pp. 65-67.

Geselowitz, David B., "On the Theory of the Electrocardiogram," Proceedings of the IEEE, vol. 77, No. 6, Jun. 1989, pp. 857-876.

Han et al., Enhanced Computer Vision, Microsoft Kinect Sensor: A Review, IEEE Transactions on Systems, Man and Cybernetics, Part B, IEEE Transactions on Cybernetics, vol. 43, No. 5, Oct. 2013, pp. 1318-1334.

Hoppe, "Introduction to Network Mathematics," 2007-2008 [online ][retrieved, on Jul. 1, 2021] Retrieved from the Internet <URL: htt:// eds hare .so ton .ac .uk/922/2/i ndex.html >.

Huiskamp et al., "Heart Position and Orientation in Forward and Inverse Electrocardiography," Med Biol Eng Comput 30, 1992, 8 pages.

Huiskamp et al., The depolarization sequence of the human heart surface computed from measured body surface potentials. IEEE Transactions on Biomedical Engineering. Dec. 1988;35(12): pp. 1047-1058. PubMed PMID: 3220498.

International Search Report and the Written Opinion of the International Searching Authority from the European Patent Office in Application No. PCT/US2017/050188 dated Nov. 7, 2017, 17 pages.

Lieberman, "Interpreting 12-Lead ECGs: A Piece by Piece Analysis" The Nurse Practitioner, vol. 33 (2008) pp. 28-35.

Liu et al., "Deformable registration of cortical structuresvia hybrid volumetric and surface warping." Neuroimage. Aug. 2004, vol. 22, No. 4, pp. 1790-1801.

Mahmoud et al., "Internospital Transfer Due to Failed Prehospital Diagnosis tor primary Percutaneous Coronary Intervention: an Observational Study on Incidence, Predictors, and Clinical Impact," European Heart Journal: Acute Cardiovascular Care 2(2), 2013, pp. 166-175.

Meijs et al., . On the Numerical Accuracy of the Boundary Element Method. IEEE Transactions on Biomedical Engineering, Oct. 1989;BME-36, vol. 10, pp. 1038-1049.

Oostendorp et al., Interpolation on a triangulated 3D surface. Journal of Computational Physics. 1989;80(2): pp. 331-343.

Poerner et al., "Physiological Range of Mechanical Synchronicity of the Human Heart: Comparison Between Different Echocardiographic Assessment Modalities," Ultrasound in Med. and Biol., vol. 31, 2005, pp. 1163-1172.

Prassl et al., "Automatically Generated, Anatomically Accurate Meshes for Cardiac Electrophysiology Problems," (IEEE Transactions on Biomedical Engineering, vol. 56, 2009, pp. 1318-1330.

Rantner et al., "Placement of implantable cardioverter-defibrillators in paediatric and congenital heart defect patients: a pipeline for model generation and simulation prediction of optimal configurations," J. Physical, vol. 591, 2013, pp. 4321-4334.

Romero et al. "Effects of the Purkinje System and Cardiac Geometry on Biventricular Pacing: A Model Study," Annals of Biomedical Engineering, vol. 38, No. 4, Apr. 2010 (2010) pp. 1388-1398.

Swihart et al., Numerical Methods for solving the forward problem in electrocardiography, The Theoretical Basis of Electrocardiology, Nelson CV, Geselowitz DB, editors. Oxford: Clarendon Press; 1976, pp. 257-293.

Van Dam et al., "A New 3D Patient Specific Morphing Tool Enabling Clinical Application of Non-lnvasive Cardiac Activation Imaging," 1 page.

Van Dam et al., "Application of the Fastest Route Algorithm in the Interactive Simulation of the Effect of Local Ischemia on the ECG", Med Biol Eng Comput 47, Published online Sep. 3, 2008, 10 pages.

Van Dam et al., "Non-lnvasive Imaging of Cardiac Activation and Recovery," Annals of Biomedical Engineering, vol. 37, No. 9, Sep. 2009, pp. 1739-1756.

Van Dam et al., "Quantitative Localization of Premature Ventricular Contractions using Myocardial Activation ECGI from the Standard 12-Lead Electrocardiogram," Journal of Electrocardiology, 2013, pp. 574-579.

Van Oosterom, A., "Genesis of the T Wave as Based on an Equivalent Surface Source Model," Journal of Electrocardiology, vol. 34S, 2001, pp. 217-227.

Van Oosterom, A., "The Equivalent Double Layer: Source Models for Repolarization," Springer-Verlag London Limited, 2011, pp. 227-246.

Van Oosterom, et al., The Influence of Heart Position and Orientation on Body Surface Potentials. Journal of Electrocardiography vol. 24, No. 3, Jul. 1991, 3 pages.

Van Oosterom, The Equivalent Surface Source Model in its Application to the T Wave, . Electrocardiology '01; 2002: Univ Press Sao Paolo, 6 pages.

Wilson et al.," The DIstrbution of the Action currents Produced by Heart Muscle and Other Excitable Tissues Immersed in Extensive Conducting Media," The Journal of General Physiology, Published Jan. 20, 1933, pp. 423-456.

Zalenski et al., "Value of Posterior and Right Ventricular Leads in Comparison to the Standard 12-Lead Electrocardiogram in Evaluation of ST-Segment Elevation in Suspecte" The American Journal of Cardiology, vol. 79, Issue 12, Jun. 15, 1997, pp. 1579-1585.

(56) References Cited

OTHER PUBLICATIONS

Zhang et al., "3-Dimensional Activation Sequence Reconstruction from Body Surface Potential Maps by Means of a Heart-Model-Based Imaging Approach," Computers in Cardiology, vol. 31, 2004, pp. 1-4.

Zhou et al., "Voxel-conding for tiling complex volumetric objects." In Proceedings the Eighth Pacific Conference on Computer Graphics and Applications. Oct. 3, 2000, pp. 307-451.

500

500

METHOD OF CARDIAC RESYNCHRONIZATION THERAPY

RELATED APPLICATIONS

This application is a continuation-in-part of U.S. patent application Ser. No. 15/695,332 entitled "System and Method for Cardiac Resynchronization" filed Sep. 5, 2017, which claimed priority to U.S. Provisional Patent Application No. 62/383,804 filed Sep. 6, 2016, the entire contents of both of which are hereby incorporated by reference. This application also claims the benefit of priority to U.S. Provisional Patent Application No. 62/888,496 entitled "Method of Cardiac Resynchronization Therapy" filed Aug. 18, 2019, the entire contents of which are hereby incorporated by reference.

BACKGROUND

Some heart defects in the conduction system result in asynchronous and/or insufficient contraction of the heart, which are sometimes referred to as conduction disorders. As a result, the heart does not pump enough blood, which may ultimately lead to heart failure. Conduction disorders can have a variety of causes, including age, heart (muscle) damage, medications and genetics.

A common cause for conduction disorders results from defects in the left and/or right ventricle fast activation fibers, the His-Purkinje system, or scar tissue. As a result, the left and right ventricles may not be synchronized. This is referred to as Left Bundle Branch Block (LBBB) or Right Bundle Branch Block (RBBB). A known way to improve heart function in case of LBBB or RBBB is cardiac resynchronization therapy (CRT), which is also known as biventricular pacing or multisite ventricular pacing. Conventionally, CRT involves simultaneous pacing of the right ventricle (RV) and the left ventricle (LV) using a pacemaker. The basic goal of CRT is to improve the mechanical functioning of the LV by restoring LV synchrony in patients with dilated cardiomyopathy and a widened QRS period, which is predominantly a result of LBBB.

Currently, the proper positioning of pacemaker leads to obtain maximum cardiac synchronization involves a certain amount of guesswork on the part of an operating physician. In particular, current methods do not allow for the determination of the optimal location for pacemaker leads, on a patient by patient basis. Further, current methods do not allow for the real time determination of whether leads have been properly positioned.

The lack of such a method may contribute to the 30% of patients that fail to respond to CRT. Accordingly, there is a need for improved cardiac imaging and stimulation methods.

SUMMARY

Various embodiments provide methods for performing cardiac resynchronization therapy and a system implementing the methods. Various embodiments may include generating, using a processing unit, a three-dimensional (3D) activation map showing the propagation of electrical signals through a heart of a patient; determining the location of a left bundle branch block (LBBB), based on the cardiac activation map; implanting a first pacing device and a second pacing device into the patient; stimulating the His Bundle of the heart, using the first pacing device; and stimulating the left ventricle (LV) of the heart, at a position downstream of the LBBB with respect to a direction of electrical conduction through the LV, using the second pacing device, after the stimulating of the His bundle.

Various embodiments may include a method of cardiac resynchronization therapy (CRT), comprising: generating, using a processing unit, a cardiac activation map comprising a three-dimensional (3D) heart model of the heart and coronary vessels of a patient and showing the propagation of electrical signals through the 3D heart model; determining the location of a left bundle branch block (LBBB) based on the cardiac activation map; implanting a first pacing device and a second pacing device into the patient; stimulating the right ventricle (RV) using the first pacing device; and stimulating the left ventricle (LV) of the heart at a position downstream of the LBBB with respect to a direction of electrical conduction through the LV using the second pacing device after stimulating the His bundle.

Various embodiments provide methods for performing cardiac resynchronization therapy and a system implementing the methods. Various embodiments may include generating, using a processing unit, a cardiac activation map comprising a three-dimensional (3D) heart model of the heart and coronary vessels of a patient and showing the propagation of electrical signals through the 3D heart model; determining the location of a right bundle branch block (RBBB) based on the cardiac activation map; implanting a first pacing device and a second pacing device into the patient; stimulating the right ventricle (RV) of the heart at a position downstream of the RBBB with respect to a direction of electrical conduction through the RV using the first pacing device; and stimulating the left ventricle (LV) of the heart using the second pacing device.

BRIEF DESCRIPTION OF THE DRAWINGS

The accompanying drawings, which are incorporated herein and constitute part of this specification, illustrate example embodiments of the invention, and together with the general description given above and the detailed description given below, serve to explain the features of the invention.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

An ECG is defined herein as any method that (preferably non-invasively) correlates actual electrical activity of the heart muscle to measured or derived (electrical activity) of the heart. In case of a classical electrocardiogram the differences in potential between electrodes on the body surface are correlated to the electrical activity of the heart. Derived ECG's can also be obtained in other ways (e.g. by measurement made by a so-called ICD (Implantable Cardioverter Defibrillator)). In order to obtain such a functional image an estimation of the movement of the electrical activity has to be provided.

Cardiac dyssynchrony has deleterious effects on cardiac function by depressing left ventricular (LV) mechanical performance, while increasing myocardial oxygen consumption. In addition, it probably causes LV remodeling. Therefore, cardiac dyssynchrony accelerates the progression of chronic congestive heart failure (CHF) and reduces patient survival.

During normal conduction, cardiac activation begins within both the left ventricular and right ventricular endocardium. In particular, electrical impulses (i.e., depolarization waves) travel substantially simultaneously through both the left and right ventricles.

Figure 1A:
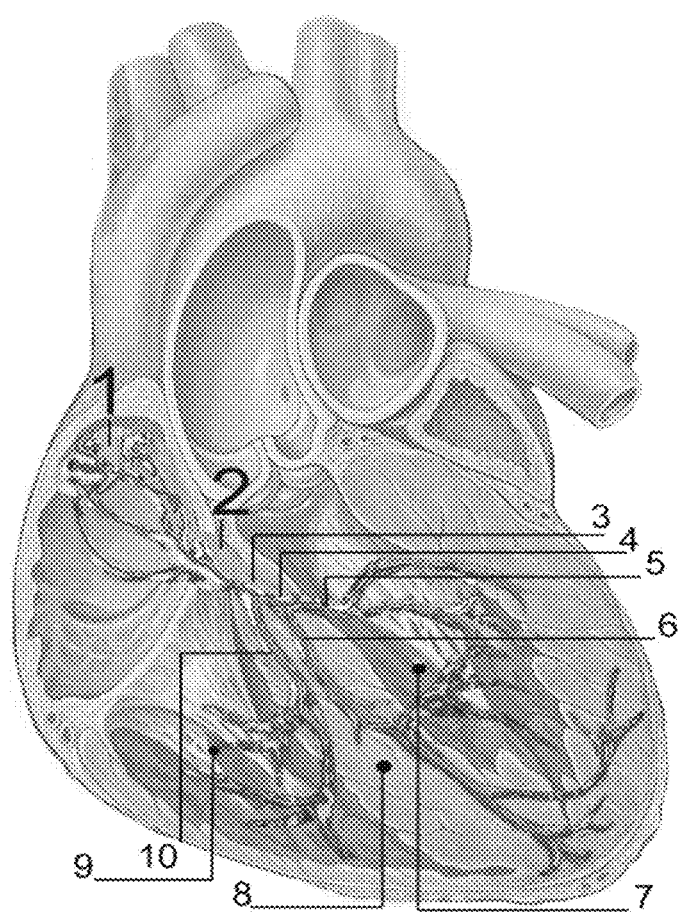
FIG. 1A is a sectional view of a human heart including the cardiac electrical conduction system.

FIG. 1A is a sectional view of a human heart including the electrical conduction system. As show in FIG. 1A, the human heart includes a sinoatrial node 1, an atrioventricular (AV) node 2, a His bundle 3, a left bundle branch (LBB) 4, a left posterior fascicle 5, a left-anterior fascicle 6, a left ventricle (LV) 7, a ventricular septum 8, a right ventricle (RV) 9, and a right bundle branch (RBB) 10.

The cardiac electrical conduction system includes heart muscle cells specialized for electrical conduction, and is situated within the myocardium. There is a skeleton of fibrous tissue that surrounds the conduction system which can be seen on an ECG. Dysfunction of the conduction system can cause irregular, fast, or slow cardiac rhythms.

The His bundle 3 is an important part of the electrical conduction system, as it transmits impulses from the AV node 2, located at the inferior end of the interatrial septum, to the left and right ventricles 7, 9. The His bundle branches into the LBB 4 and the RBB 10, which run along the interventricular septum. The LBB 4 further divides into the left posterior fascicle 5 and the left-anterior fascicle 6. These bundles and fascicles give rise to thin filaments known as Purkinje fibers. The Purkinje fibers distribute the impulse to the LV 7 and RV 9. The ventricular conduction system comprises the bundle branches 4, 10 and Purkinje networks. It takes about 0.03-0.04 seconds for the impulse to travel from the His bundle 3 to the LV 7 and RV 9.

Disorders affecting the cardiomyocytes that make up the electrical conduction system of the heart are called heart blocks. Heart blocks are separated into different categories based on the location of the cellular damage. Damage to any of the conducting cells in or below the His bundle are collectively referred to as "infra-Hisian blocks." To be specific, blocks that occur in the right or left bundle branches 4, 10 are called "bundle branch blocks," and blocks that occur in either the left anterior or the left posterior fascicles 5, 6 are called "fascicular blocks," or "hemiblocks." The conditions in which both the RBB 10 and either the left anterior fascicle 6 or the left posterior fascicle 5 are blocked are collectively referred to as bifascicular blocks, and the condition in which the right bundle branch 10, the left anterior fascicle 6, and the left posterior fascicle 5 are blocked is called trifascicular block. Infra-hisian blocks limit the heart's ability to coordinate the activities of the atria and ventricles, which usually results in a decrease in its efficiency in pumping blood.

Herein the term "pacing device" may refer to one or more micro-pacemakers or pacemaker connected to leaded electrodes. A pacemaker is an electronic device, approximately the size of a pocket watch, which senses intrinsic heart rhythms and provides electrical stimulation to electrodes attached to tissues in particular locations when indicated. A micro-pacemaker (or leadless pacemaker) is a pacemaker of reduced size that stimulates the heart without electrical wires.

Permanent pacing is most commonly accomplished through transvenous placement of leads to the endocardium (i.e., right atrium or ventricle) or epicardium (i.e., the LV surface via the coronary sinus), which are subsequently connected to a pacing generator placed subcutaneously in the infra-clavicular region. However, miniaturized pacemakers (i.e., leadless micro-pacemakers) have been developed for implantation directly on or in the heart. Accordingly, the present disclosure encompasses endocardial and epicardial pacing, which may be accomplished using pacing electrodes connected to a pacing generator and/or implantable leadless micro-pacemakers.

Cardiac resynchronization therapy (CRT) is a specialized type of pacemaker therapy that provides biventricular pacing. CRT is carried out with or without the use of an implantable cardioverter-defibrillator (ICD), a device employed for treatment and prophylaxis in patients at risk for ventricular tachycardia (VT) or ventricular fibrillation (VF).

Conventionally, CRT is performed by pacing methods, such as apical pacing for example, in which electrodes are placed on one or more points on one or both ventricles to stimulate the cardiac muscle and increase cardiac synchronicity. For example, the stimulation points (i.e., lead placements) may be based on a difference between LV and RV activation times, earliest and/or latest activation of the LV and/or RV, a detected depolarization wave blockage, or the like. The process of determining placement locations for pacing leads may include the use of a patient-specific cardiac activation map showing a three-dimensional (3D) model of the electrical activation of the patient's heart.

To increase the likelihood for CRT to be successful, the LV and RV pacing electrodes should be placed in optimal locations and the delay between the RV and LV pacing pulses should be set with the goal to shorten the QRS duration for achieving ventricular synchrony.

Figures 1B, 1C:
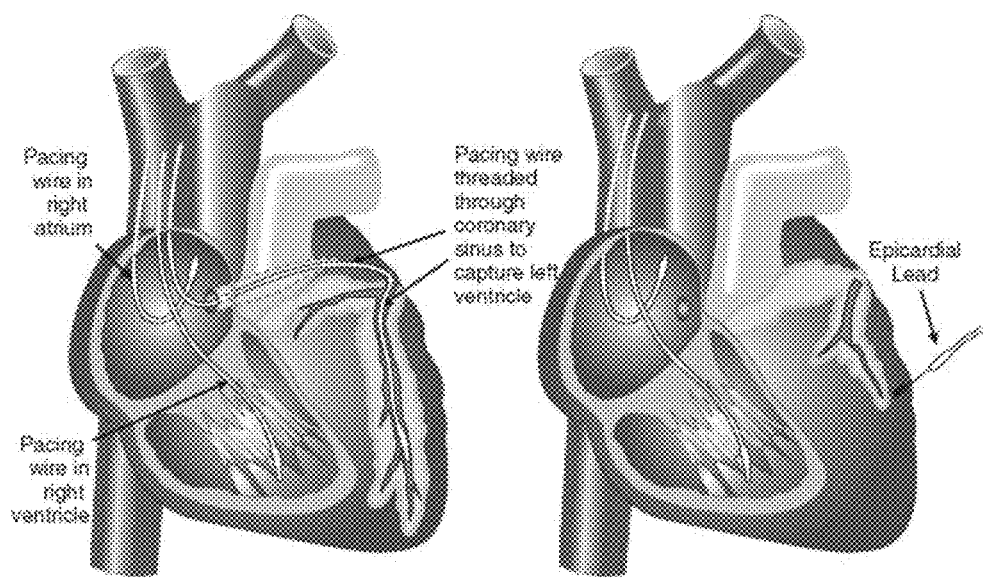
FIGS. 1B and 1C are sectional views of human hearts showing pacemaker lead locations for CRT.

FIGS. 1B and 1C show the conventional locations for CRT pacing electrodes. As shown in FIGS. 1B and 1C, a pacing electrode is placed in the RA and at the apex of the RV to stimulate the right side of the heart. To stimulate the LV, an electrode may be threaded through the coronary sinus (FIG. 1B), or may be disposed on the epicardial surface of the LV (FIG. 1C) in order to stimulate the LV. For both FIGS. 1B and 1C, the RA lead provides right atrial pacing.

However, CRT may not be effective in about one third of patients. Direct His bundle pacing (DHBP) has been studied as a potential alternative to conventional CRT pacing. In particular, DHBP involves the direct stimulation of the His-Purkinje tissue of the heart, which may produce a more synchronous ventricular depolarization and improved cardiac function as compared to right ventricular apical pacing. Further, in the long-term, DHBP has been shown to result in a reduction of left ventricular dimensions and heart failure hospitalization, and improved cardiac function. Accordingly, DHBP may be utilized for CRT in place of right ventricular apical pacing. In addition, in view of the improved cardiac function provided thereby, DHBP may also be used as a treatment for congestive heart failure.

The His bundle is formed of conduction fibers that extend through the cardiac septum. If the His bundle is not stimulated directly, only the surrounding tissue will be stimulated. In other words, such stimulation will not increase cardiac synchronicity. As such, a stimulation lead should be precisely positioned to directly stimulate the His bundle for DHBP to be effective.

If a patient has a BBB, direct His pacing and left ventricular apical pacing may not be completely effective in resynchronizing the ventricles. In particular, a pacing signal may be delayed or blocked at the site of a BBB, preventing proper cardiac function and/or resynchronization.

According to various embodiments of the present disclosure, methods of CRT are provided that include generating a cardiac activation map showing the electrical activation pattern on a three-dimensional (3D) model of a heart in order to identify the origin or cardiac activation and/or conduction delays caused by BBBs, such as a LBBB in particular.

Based on the cardiac activation sequence shown in the cardiac activation map, pacing locations on the His bundle and/or the LV can be identified that are predicted provide maximum levels of resynchronization. The locations may be highlighted on the cardiac activation map to facilitate electrode placement.

Figure 2:
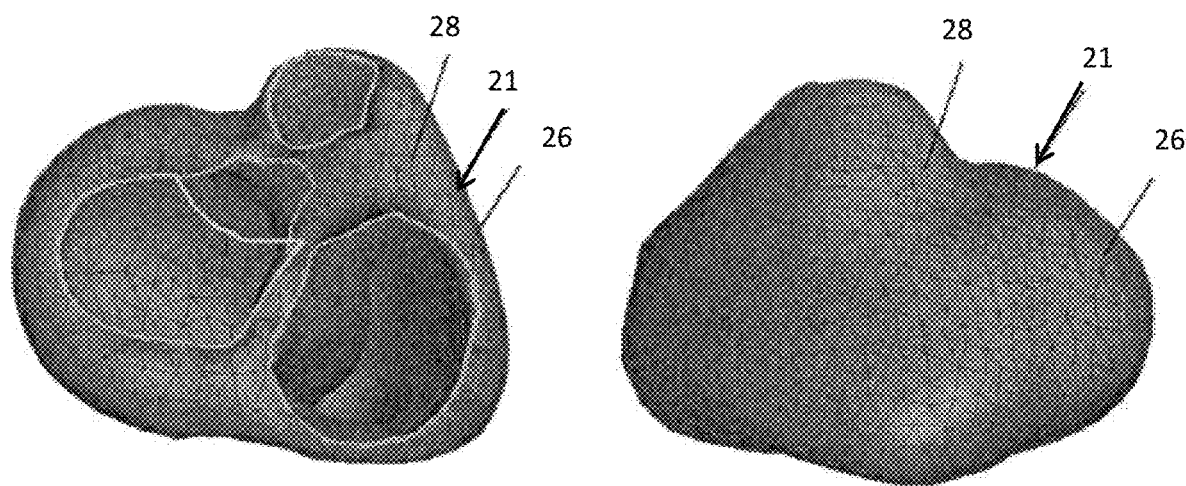
FIG. 2 is an example of a three-dimensional model of a heart.

FIG. 2 shows a three-dimensional (3D) model 21 of a heart seen in two different directions. The 3D model 21 includes a mesh 26 representing an outer surface of the heart, here the myocardial surface. In this example the 3D model also may include the septal wall. The mesh 26 has a plurality of nodes 28. In this example, the mesh 26 is a triangular mesh in which the surface of the heart is approximated by adjoining triangles.

Figure 3A:
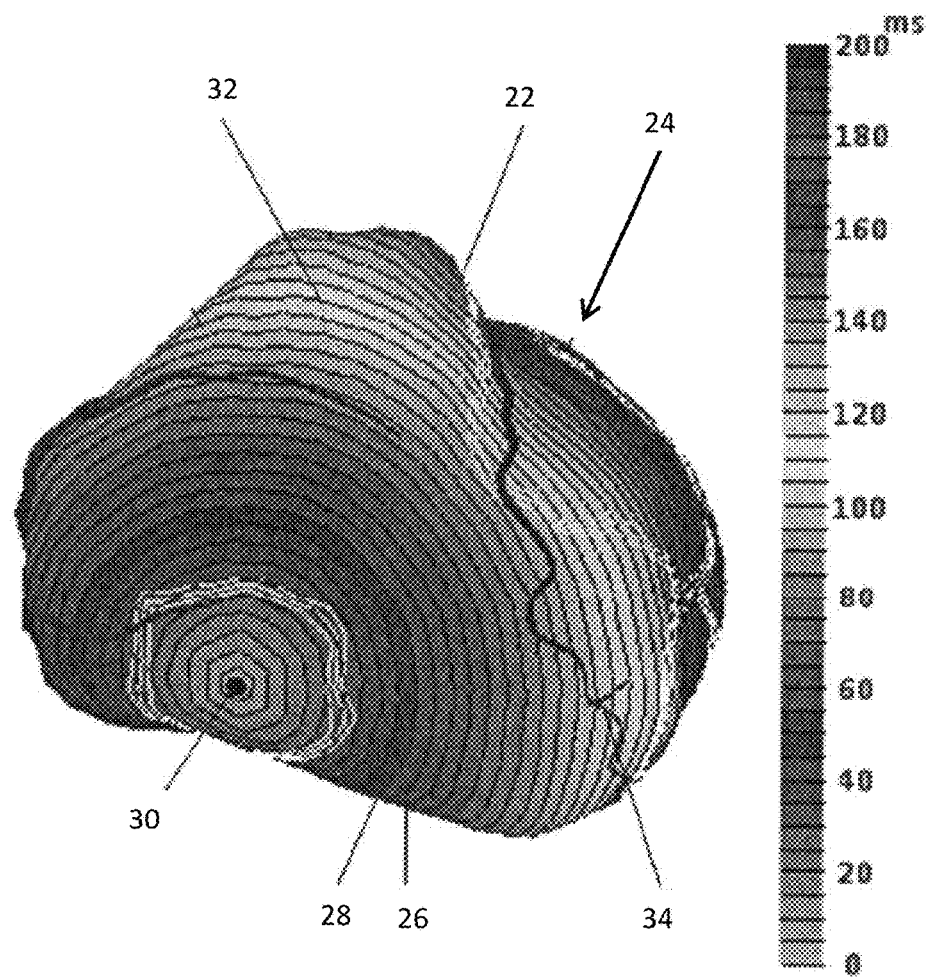
FIG. 3A is a plan view of a 3D model of electrical activation of a heart.

FIG. 3A is a 3D activation map 24 showing the initial electrical activation of a heart from a single stimulation location 30. In particular, FIG. 3A shows a ventricular surface of the myocardium with a septal wall 22. In general, the activation map 24 may include a mesh 26 representing a ventricular surface of the heart, here an outer surface of the ventricular myocardium with septal wall 22 as represented in FIG. 2. The mesh 26 has a plurality of nodes 28. In the illustrated example, the heart is electrically stimulated at a stimulation location 30. Upon electrical stimulation at the stimulation location 30, the electrical signals will travel through the heart tissue. Hence, different parts of the heart will be activated at different times. Each location on the heart has a particular delay relative to the initial stimulation. Each node 28 has associated therewith a value representative of a time delay between stimulation of the heart at the stimulation location 30 and activation of the heart at that respective node 28. Locations that share the same delay time are connected by isochrones 32 in FIG. 3A.

Herein, isochrones are defined as lines drawn on a 3D heart surface model connecting points on this model at which the activation occurs or arrives at the same time. The delay time for nodes across the heart surface in this example is also displayed by differing rendering colors. The vertical bar indicates the time delay in milliseconds associated with the respective colors. The stimulation location 30 can be the location of intrinsic activation of the heart. In other embodiments, the stimulation location 30 may be disposed on the His bundle.

Figure 4:
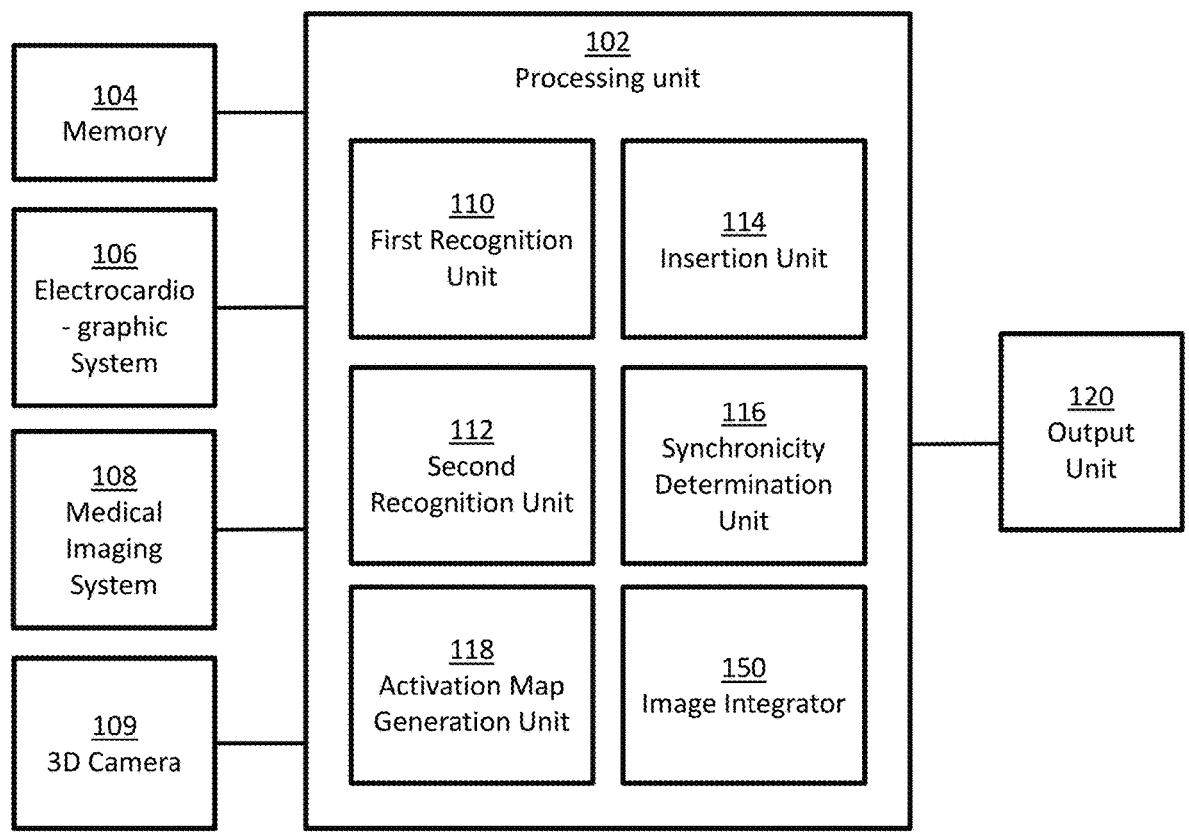
FIG. 4 is a schematic representation of a cardiac imaging system according to various embodiments of the present disclosure.

FIG. 4 is a schematic representation of a system 100 for providing a representation of synchronicity of electrical activation of heart tissue. The system 100 includes a processing unit 102 and a memory 104.

The 3D activation map 24 can be obtained by combining electrocardiographic and medical imaging data. This data may be stored in the memory 104. The processing unit 102 may be connected to an electrocardiographic system 106, a medical imaging system 108, and a 3D camera 109, for retrieving the data and storing corresponding data in the memory 104. An electrocardiographic imaging (ECGI) method able to determine the cardiac activation from a 12 lead ECG may be applied by the processing unit 102 for determining the 3D activation map 24 of electrical activation of the heart. The ECG signals may be combined with a patient-specific 3D anatomical model of the heart, lungs, and/or torso, in order to compute the positions of the cardiac isochrones. The patient-specific 3D anatomical model may be obtained from a magnetic resonance image (MRI) or computed tomography (CT) images. Alternatively or additionally, a 3D anatomical model showing closest conformity to the patient may be selected, and optionally modified, from a database including a plurality of 3D anatomical models. The selected, and optionally modified, 3D anatomical model may serve as the patient-specific 3D anatomical model.

The 3D activation map 24 may also include further information. In the example of FIG. 3A, the 3D activation map 24 may include cardiac blood vessels 34, veins on the myocardium. In some embodiments, the activation map 24 may include detailed representations of internal cardiac features, such as the His bundle, fibrous tissue that surrounds the His bundle, the AV junction, and/or the cardiac septum. This information may be added to the activation map 24 with nodes indicated as being associated with such cardiac features. Optionally, the processing unit 102 may include a first recognition unit 110 arranged for automatically retrieving information representative of the location of such cardiac features from the patient's 3D anatomical model of the heart. The processing unit 102 may then automatically insert this information into the activation map 24.

The activation map 24 may also include information on scar tissue. Scar tissue locations may be obtained from delayed enhancement MRI images and added to the activation map 24. Scar tissue can be simulated in the activation map 24 by reducing the propagation velocity of electrical signals there through. Scar tissue can also be accounted for by selling the transition from one node to another to very slow or non-transitional for the areas in the heart wall where scar tissue is present. Optionally, the processing unit 102 may include a second recognition unit 112 arranged for automatically retrieving information representative of the location of such scar tissue from the patient-specific three-dimensional anatomical model of the heart. The processing unit 102 may then automatically insert this information into the activation map 24.

In various embodiments, the obtained activation map 24 may be used for obtaining further information on electrical activation of the heart. For example, the time delay of activation from one node to another may be determined. This may be used to generate, on the basis of the activation map 24, other views resulting from initial stimulation at other nodes of the mesh 6. Thereto, the processing unit 102 may include an insertion unit 114. The insertion unit 114 may take the activation map 24 and define a certain node as a stimulation location. The activation map 24 may assume stimulation at a predetermined node. The insertion unit 114 may remove stimulation at that predetermined node for calculation purposes.

Figure 3B:
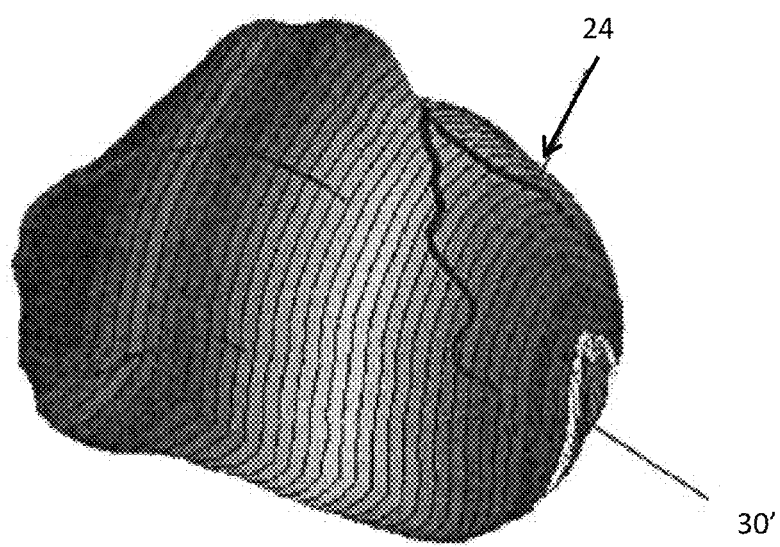
FIG. 3B is a plan view of a 3D model of electrical activation of a heart.

FIG. 3B shows an example resulting from initial stimulation at another stimulation location 30'. A view resulting from initial stimulation at other nodes of the mesh 26 may be generated for each node of the mesh 26.

A particular electrical activation sequence of the entire heart, resulting from stimulation at a particular node, may be summarized in a single parameter, namely, heart activation synchronicity. The heart activation synchronicity provides an indication of how synchronously the entire heart is activated. For common situations, a more synchronous activation of the heart is considered beneficial. The measure for heart activation synchronicity in this example is standard deviation (std) of the depolarization (dep) times of the heart. Hence, the heart activation synchronicity provides an indication of synchronicity of activation of the entire heart as a result of stimulation at the respective node. The processing unit 102 may include a synchronicity determination unit 116 configured to determine the heart activation synchronicity.

In various embodiments, the heart activation synchronicity may be determined separately for stimulation at each node. Hence, a measure of heart activation synchronicity for each node of the mesh may be provided. The processing unit 102 may include a cardiac activation map generation unit 118 configured to generate a cardiac activation map based on the calculation of the heart activation synchronicity for each node, by the synchronicity determination unit 116. The processing unit 102 may be connected with an output unit 120 arranged for outputting the cardiac activation map and/or alternative data to a user. The output unit 120 may be a display unit, a printer, a messaging unit, or the like.

Figure 3C:
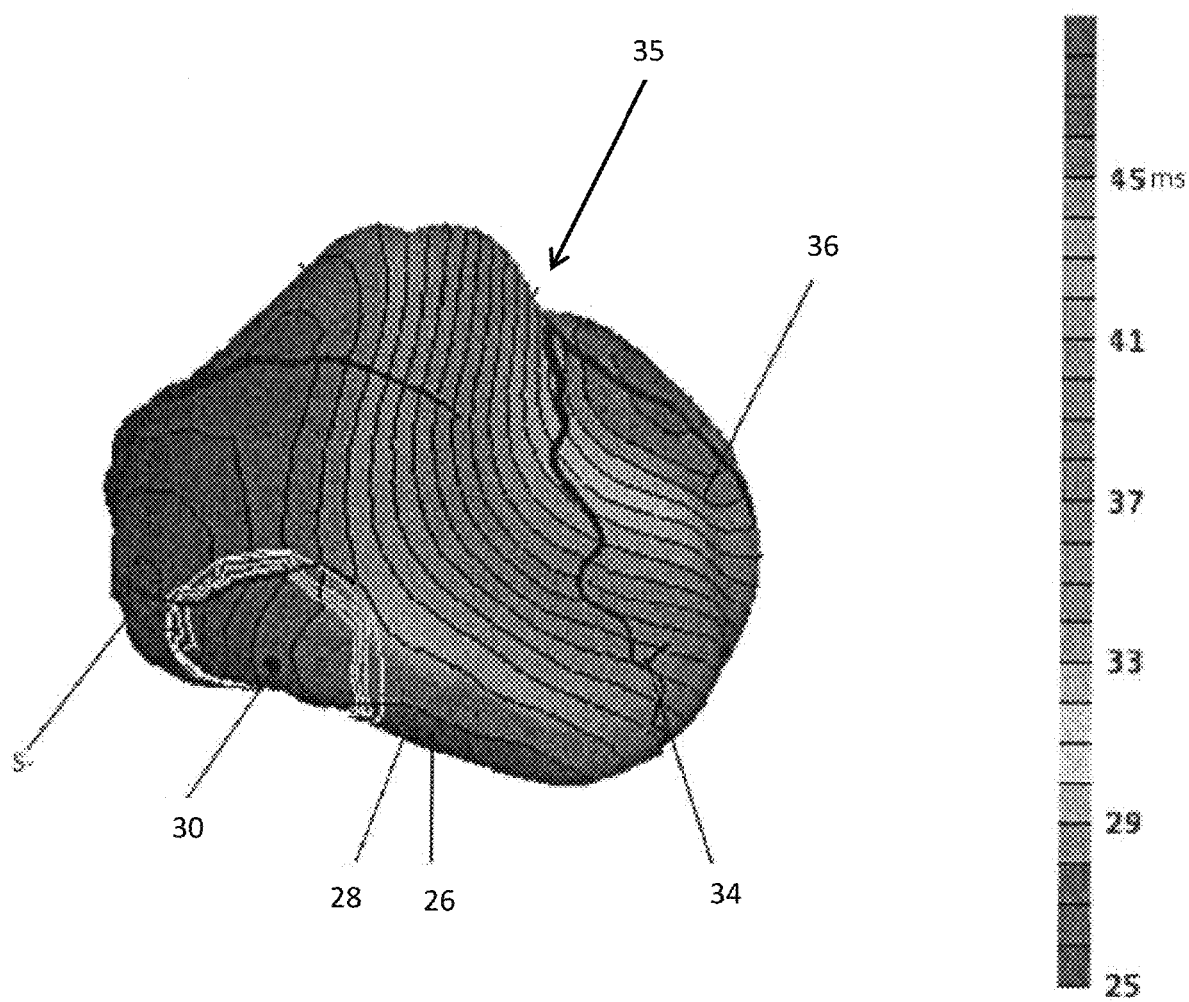
FIG. 3C is a plan view of an activation map according to various embodiments of the present disclosure.
Figure 3D:
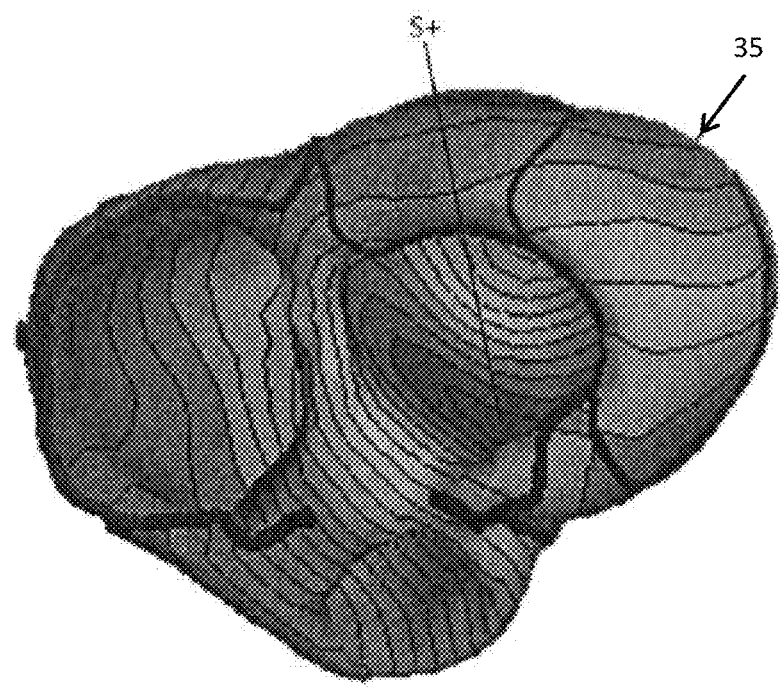
FIG. 3D is a plan view of an activation map according to various embodiments of the present disclosure.

FIG. 3C shows an example of a cardiac activation map 35. In FIG. 3C, heart activation synchronicity is indicated for each node in the activation map 35. In this example, the indication may be show by providing false colors and/or iso-sync lines 36. The iso-sync lines 36 connect nodes having the same heart activation synchronicity. The activation map 35 provides a singular 3D overview showing which locations on the heart result in good heart activation synchronicity, and which locations on the heart result in poor heart activation synchronicity, if the heart were stimulated at such locations. In this example, it can be seen that the original stimulation location 30 does not provide particularly good synchronization, with a heart activation synchronicity value of approximately 45 ms standard deviation of the depolarization times of the heart. The least favorable stimulation location, here the location with the highest heart activation synchronicity value, is indicated at S–. In this example, the most favorable stimulation location, where the lowest heart activation synchronicity value occurs, is indicated at S+. It is noted that the most favorable stimulation location S+ may best be seen when looking at the cardiac activation map 35 from another direction, as shown in FIG. 3D.

Another example of a measure for heart activation synchronicity is a range in depolarization times (maximum depolarization time-minimum depolarization time). The range in depolarization times may be corrected for cycle length. Another example of a measure for heart activation synchronicity is a standard deviation of the LV depolarization times only. Another example of a measure for heart activation synchronicity is a delay between stimulus and septum activation. Another example of a measure for heart activation synchronicity is an AV delay. Another example of a measure for heart activation synchronicity is a VV delay. The measure for heart activation synchronicity may be chosen in dependence of the task at hand and/or in dependence of a specific condition or abnormality experienced in the patient.

Figure 5A:
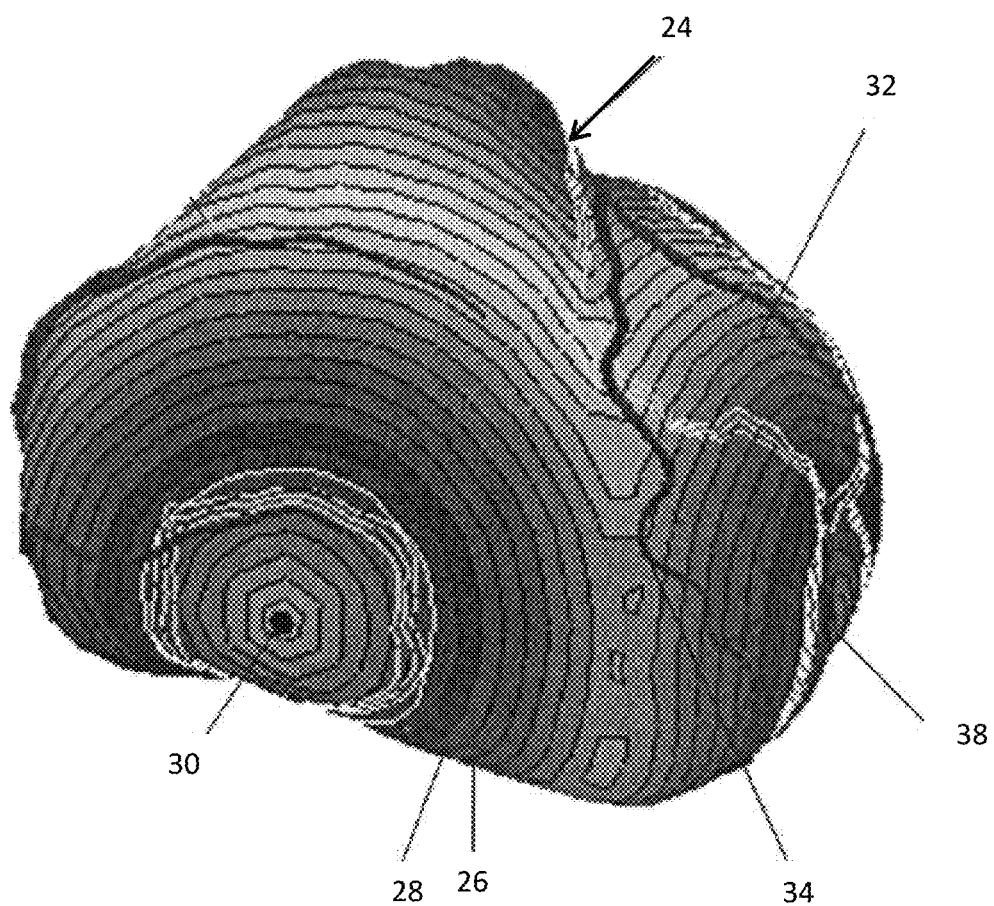
FIGS. 5A and 5B are plan views of 3D models of the electrical activation of a heart according to various embodiments of the present disclosure.

In FIG. 5A, a second example is shown in which a second stimulation location 38 is defined. Then electrical activation of the heart is calculated using the activation map 24 and simultaneous stimulation at the first stimulation location 30 and the second stimulation location 38. In this example, the insertion unit 114 does not remove stimulation at the first location 30 for calculation purposes. FIG. 5A shows the calculated resulting electrical activation of the heart. The total activation time shortens due to the addition of the second stimulation location 38. In this example, the first stimulation location 30 represents the location of intrinsic activation of the heart, or a first chosen location to stimulate or a stimulation generated by an already present pacemaker lead within the heart.

Figure 5B:
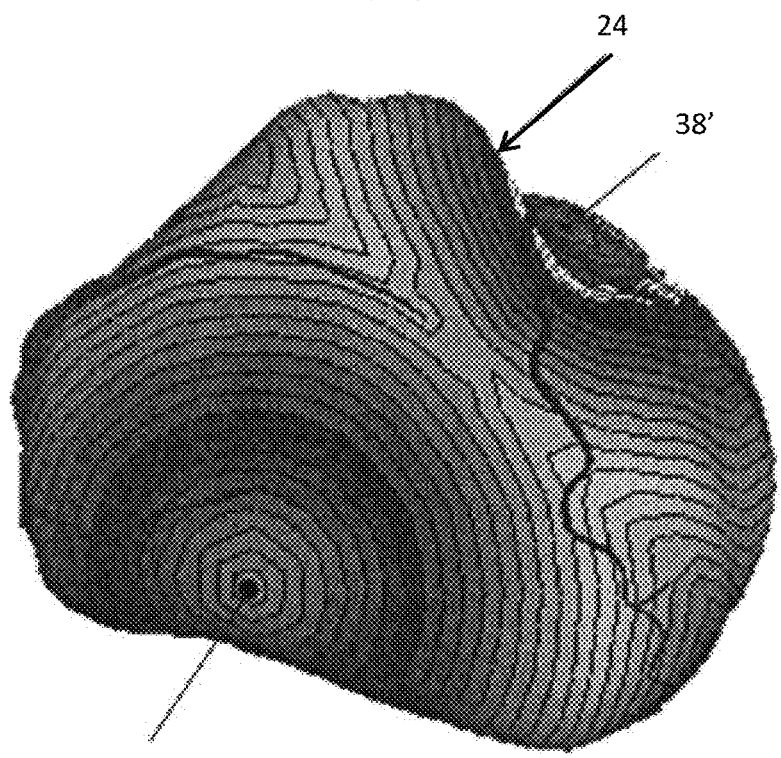

FIG. 5B shows an example resulting from initial stimulation at a second stimulation location 38' simultaneous with stimulation at first stimulation location 30. A view resulting from initial stimulation at second nodes of the mesh 26 simultaneous with stimulation at a first node associated with the first stimulation location 30 may be generated for each node of the mesh 26.

Figure 5C:
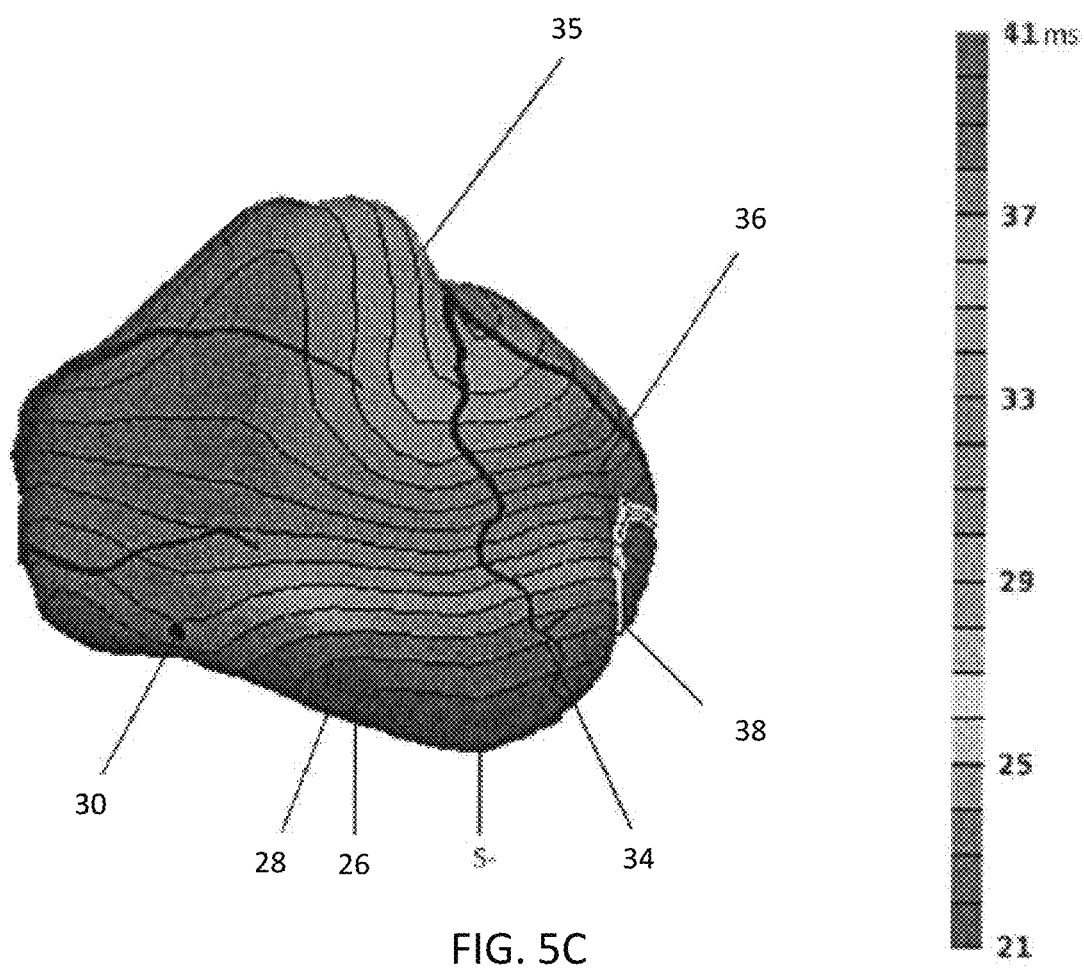
FIGS. 5C and 5D are plan views of cardiac activation maps according to various embodiments of the present disclosure.
Figure 5D:
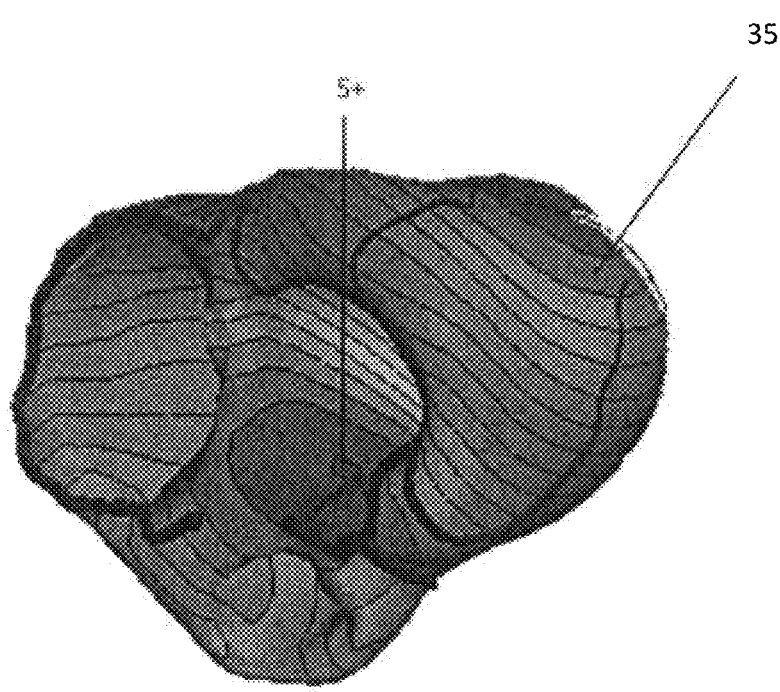

In the example of FIGS. 5C and 5D, a particular electrical activation sequence of the entire heart is combined and shown as the heart activation synchronicity. In this example, the electrical activation sequence involves stimulation at the second stimulation location 38 simultaneous with stimulation at the first stimulation location 30. The heart activation synchronicity again provides an indication of how synchronous the entire heart is activated. In some embodiments, the heart activation synchronicity may be determined separately for stimulation at each node simultaneously with stimulation at the first 30 and second 38 stimulation locations. This provides a measure of heart activation synchronicity for each node acting as third stimulation location of the mesh 26.

FIG. 5C shows an example of a heart activation map 35 showing which locations on the heart result in good heart activation synchronicity and which location on the heart result in poor heart activation synchronicity. If the heart were stimulated at such locations simultaneous with stimulation at the first stimulation location 30 and the second stimulation location 38. In this example, the least favorable third stimulation location S− had the highest heart activation synchronicity value of approximately 41 ms, when the first stimulation location 30 and the second stimulation location 38 were stimulated simultaneously. In this example, the most favorable third stimulation location S+ had the lowest heart activation synchronicity value, when with the first stimulation location 30 and the second stimulation location 38 were stimulated simultaneously. It is noted that the most favorable stimulation location S+ may best be seen when looking at the activation map 35 from another direction, as shown in FIG. 5D.

Figure 6:
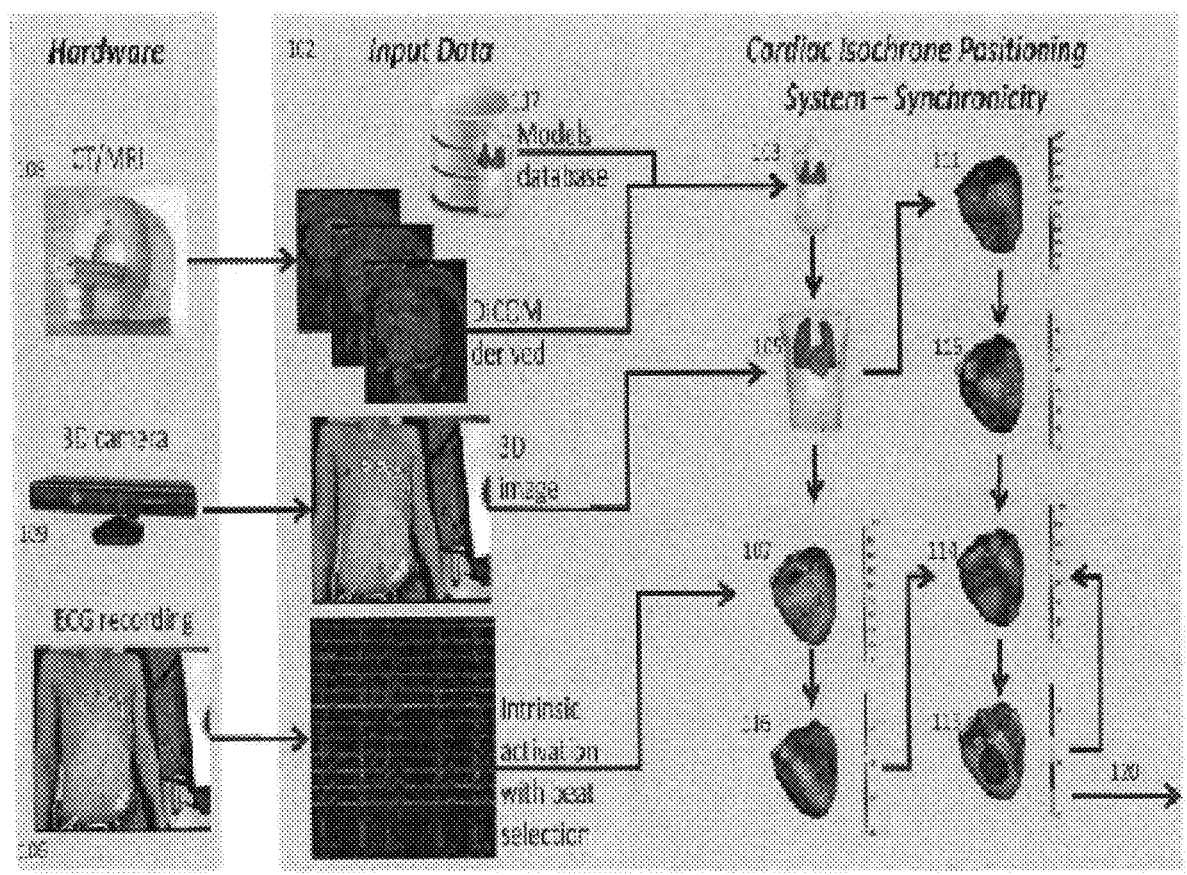
FIG. 6 is a schematic representation of a cardiac imaging system according to various embodiments of the present disclosure.
Figure 7:
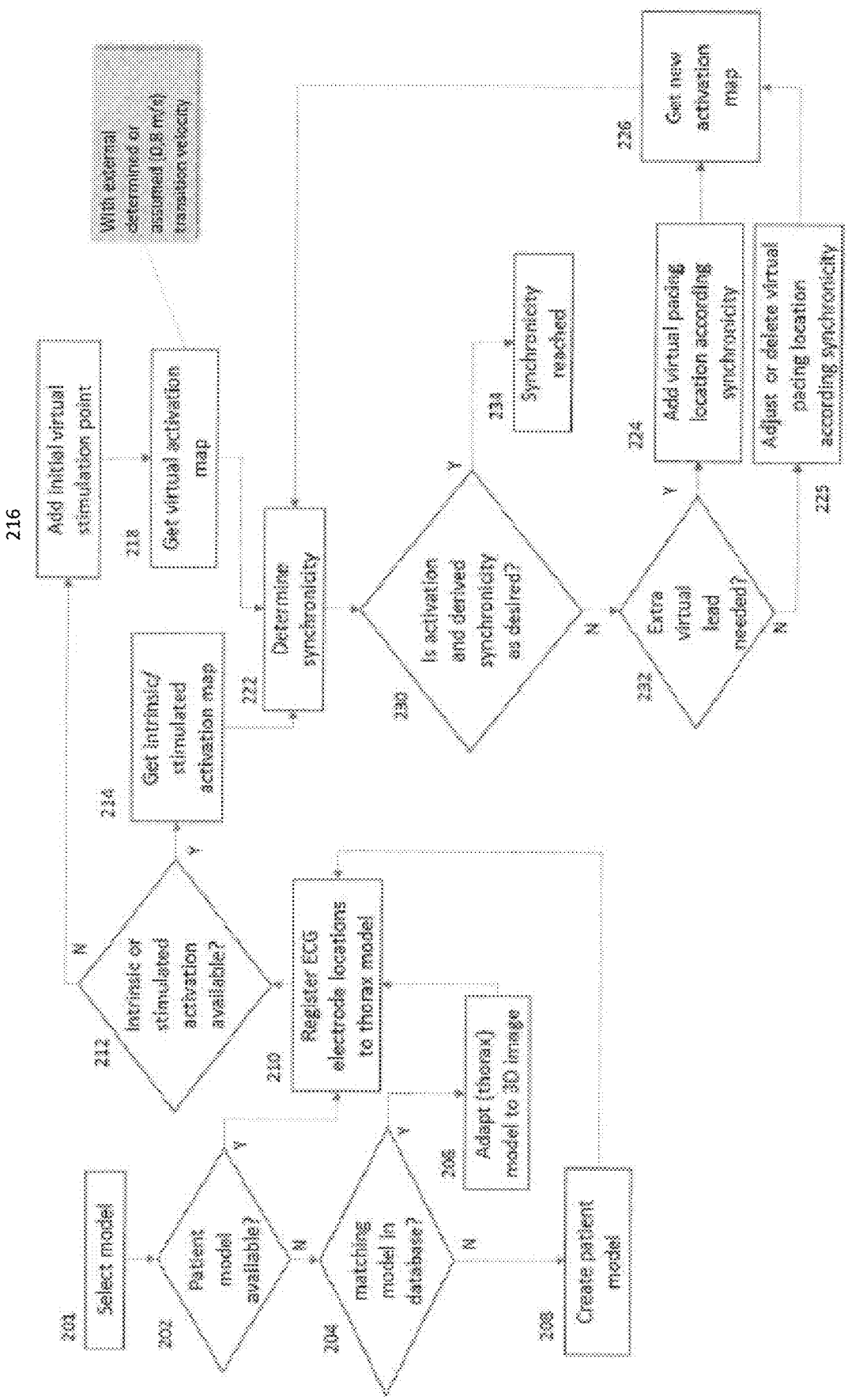
FIG. 7 is a flow chart illustrating a method according to various embodiments of the present disclosure.

FIG. 6 shows another schematic representation of a system 100 for providing a cardiac activation map. FIG. 7 illustrates a method of determining heart synchronicity using the system 100 according to an embodiment. Referring to FIG. 6, the system includes a processing unit 102 which receives data from hardware modules. Optionally the processing unit 102 may receive ECG data from an electrocardiographic system 106. The processing unit may receive patient-specific anatomical data from a medical imaging system 108. In some embodiments, the anatomical data may include detailed representations of internal cardiac features, such as the His bundle, fibrous tissue that surrounds the His bundle, the AV junction, and/or the cardiac septum. Optionally, the processing unit 102 may receive information on the positions of ECG leads relative to the anatomy of the patient from a 3D camera 109, such as a 3D image and the torso model mapped to the 3D image. ECG lead positions may also be entered into the system manually.

From the patient-specific anatomical data, the processing unit 102 may determine the cardiac activation map. The processing unit 102 may include the following units, and may perform the operations illustrated in FIG. 7 and described below to generate a cardiac activation map. In particular, the processing unit 102 may use a patient-specific 3D anatomical model of the thorax of the patient and the size, orientation, and location of the heart within the thorax. Such a model may be selected in step 201 for further use by the processing unit. Such model may already be available in step 202. If the model is not yet available, a retrieval unit 103 may check whether a suitable anatomical model for this patient is present in a database 117 in step 204. If so, the retrieval unit 103 may retrieve the suitable anatomical model from the database 117.

In step 206, the retrieval unit 103 may adapt the anatomical model from the database to the 3D image of the patient so as to transform the selected anatomical model into a (quasi) patient-specific 3D anatomical model. If no suitable patient-specific anatomical model is available in the database 117, the retrieval unit 103 may generate the patient-specific anatomical model on the basis of the received patient-specific anatomical 3D image data in step 208.

Optionally, the patient-specific 3D model also may include the size, orientation and/or location of other structures in the patient, such as the lungs and/or other organs. The patient-specific 3D model may be a volume conductor model.

Using the positions of ECG leads and the patient-specific model, a lead locator module 105 may determine corresponding positions of the ECG leads in the patient-specific 3D model, to provide an enhanced patient-specific model in step 210.

In step 212, when the patient-specific anatomical model and/or the enhanced patient-specific model available, a determination is made as to whether ECG data representative of intrinsic or stimulated activation is available. In step 214, if intrinsic activation data or pacing stimulation from one or more already present pacemaker leads is available, an activation unit 107 may generate a 3D electrical conduction model (e.g., activation map) showing the current activation of the heart of the patient, on the basis of the patient-specific model and the ECG data.

If no ECG data on intrinsic or stimulated activation is available, a virtual stimulation unit 111 may add an initial virtual stimulation to an electrical model of the heart based on previously determined and/or assumed transition velocities between nodes in step 216. An assumed transition velocity may be 0.8 ms, for example. The electrical model may include arteries, veins, and/or scar tissue as explained above. In step 218, a 3D electric model of virtual activation of the heart of the patient may be generated.

From the 3D activation model of intrinsic, stimulated, or virtual activation of the heart of the patient, a synchronicity determination unit 116 may generate a cardiac activation map 35 in step 222, as described above. On the basis of the cardiac activation map, the processing unit 102 may determine whether the artificial stimulation location or virtual stimulation location resulted in optimal activation and synchronicity in step 230. If so, the processing unit 102 may calculate optimal stimulation locations for a patient's heart in step 234.

If it is determined in step 230 that optimum synchronicity has not been reached, the method proceeds to step 232 in which it is determined whether an extra virtual stimulation location should be added, or if a virtual stimulation location should be moved or changed with respect to the timing parameters. This determination may be made by a clinician, by the processing unit, or by the clinician based on information or recommendations presented on a display by the processing unit. If it is determined that a virtual stimulation location should be moved or changed, the artificial or virtual stimulation location may be adjusted accordingly in step 225. In step 226, activation may be determined again. Synchronicity may then be recalculated in step 222. The process may be repeated until a desired activation is determined to be achieved in step 230.

The system may also virtually adapt the current artificial stimulation locations (i.e., pacemaker lead locations) with respect to its current stimulation parameters to reach optimum synchronicity.

The system may also be used for assessing multiple stimulations. The multiple stimulations may be a combination of intrinsic activation and stimulated activation (pacing). The multiple stimulations may be multiple stimulated pacing, for example. The user, the processing unit 102, or the clinician based on information or recommendations presented on a display by the processing unit may determine in step 232 whether an additional stimulation location (e.g., an additional pacemaker lead) would be desirable.

If an additional stimulation location is desired, an additional stimulation location may be inserted by the insertion unit 114. Then activation for the situation with the original stimulation location and the added virtual stimulation location may be determined again in step 226, and synchronicity may be recalculated in step 222. On the basis of the cardiac activation map, the processing unit 102 may determine in step 230 whether the additional virtual stimulation location resulted in optimum synchronicity. If the optimum synchronicity has not been reached, the method proceeds to step 232, in which it is determined whether an extra virtual stimulation location should be added, or if a virtual stimulation location should be moved or removed, with respect to the timing parameters. In such a case, the process may be repeated one or more times.

Based on the patient specific cardiac activation model, a cardiac synchronicity model may be generated. The synchronicity model may be a 3D heart surface model including iso-sync lines. In the synchronicity model, the iso-sync lines represent the activation synchronicity of the heart. This synchronicity may be based on specific activation conditions, such as right ventricle activation at a lead position of a pacemaker.

As an example, the synchronicity model may be generated as follows. The activation isochrones for the intrinsic LBBB pattern may be determined in the following steps.

1A) A patient-specific anatomical 3D model of the heart, lungs, and thorax may be generated, e.g. on the basis of an MRI or CT image of the patient, or derived from a model taken from a database adapted to the patient's dimensions, e.g. with use of the 3D camera. The anatomical 3D model may e.g. include a 3D surface model of the heart, a 3D surface model of the lungs and a 3D surface model of the thorax. A 3D surface model may be a close approximation of the actual surface, by means of a mesh of a plurality of polygons, such as triangles, connected at their corners. The interconnected corners form nodes of the mesh.

In some embodiments, the anatomical 3D model may include detailed depictions of the His bundle and adjacent structures, such as the AV junction and cardiac septum. For example, the His bundle may be identified by detecting the fibrous tissue that surrounds the His bundle using ECG, MRI, and/or CT imaging data.

1B) An ECG, e.g. a 12-lead ECG, may be measured. The exact locations of the electrodes of the ECG device on the thorax may be recorded. The positions of the electrodes in the 3D anatomical model are used for estimating the distribution, fluctuation, and/or movement of electrical activity through heart tissue. The exact locations of the recording leads or the ECG device may be entered in the anatomical 3D representation of the thorax.

1C) Optionally, scar tissue and/or coronary vessels may be incorporated in the anatomical 3D representation of the heart. The presence and location of scar tissue may be derived from delayed enhancement MRI images.

1D) The measurements per recording lead of the ECG device may be related to the heart and torso geometry. Using an inverse procedure, the intrinsic activation may be determined. The distribution, fluctuation, and/or movement of electrical activity through heart tissue may be based upon a myocardial distance function, a fastest route algorithm, shortest path algorithm, and/or fast marching algorithm.

2) Once the activation isochrones for the intrinsic LBBB pattern have been determined, a stimulus site may be added to the intrinsic activation for each node on the heart and the desired synchronicity of the heart may be computed from the outcome. A "node" refers to an intersection point of the triangles of upon which the anatomical 3D heart model is based.

The above methods may also be used to determine optimal location(s) for placement of cardiac pacemaker electrode(s). To determine the optimal pacing site(s), activation maps may be computed. The intrinsic activation map, in combination with a determined stimulation point(s) may be applied to a new cardiac isochrone positing map.

Bundle Branch Block Identification

Figure 8A:
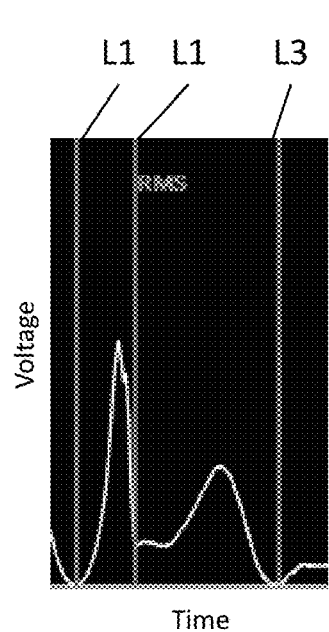
FIG. 8A shows the ECG pattern of one beat of a heart.
Figure 8B:
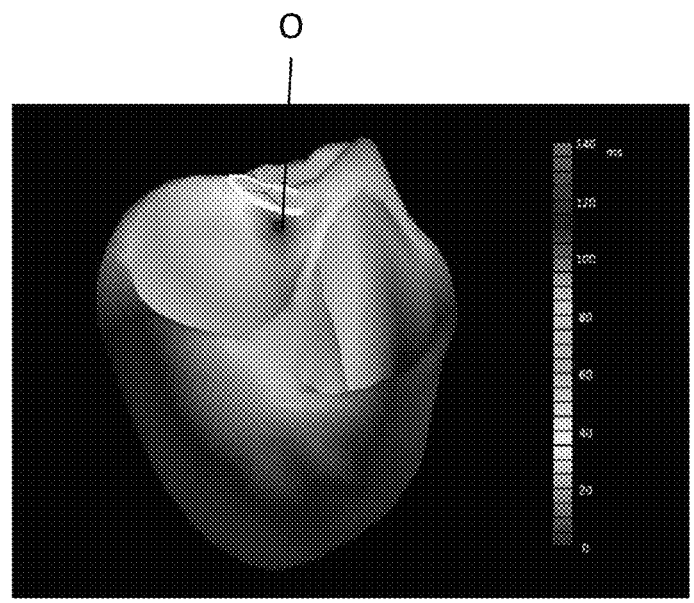
FIG. 8B is an example of a 3D cardiac activation map of LBB activation patterns of the heart during the beat.
Figure 8C:
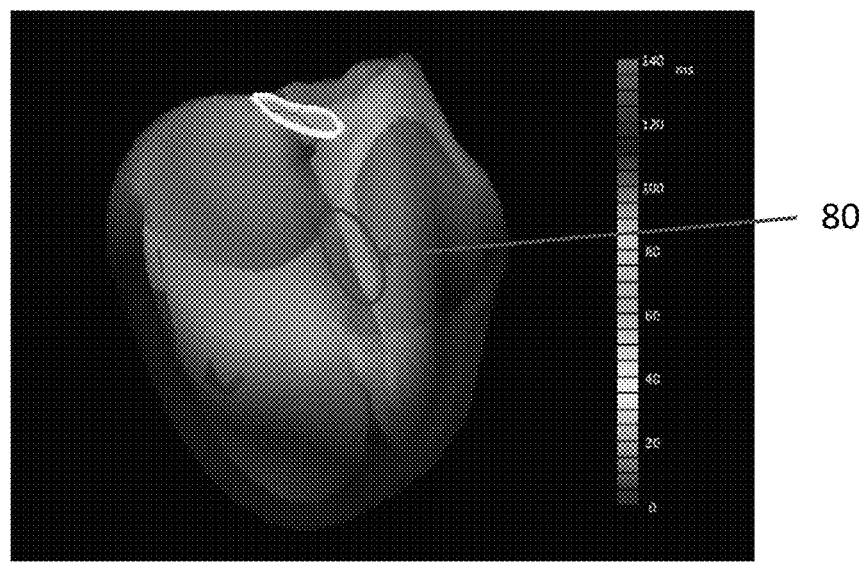
FIG. 8C is a sectional view of 3D cardiac activation map of FIG. 8B showing a conduction delay indicating the location of a LBBB.

FIG. 8A shows the ECG pattern of one beat of a heart, FIG. 8B is an example of a 3D cardiac activation map of LBB activation patterns of the heart during the beat, and FIG. 8C is a sectional view of 3D synchronization map of FIG. 8B, showing a conduction delay 80 indicating the location of a LBBB.

Referring to FIG. 8A, red line L1 indicates the start of the Q wave, blue line L2 indicates the end of the S wave, and green line L3 indicates the end of the T wave. As shown in FIG. 8B, a cardiac activation map corresponding to the ECG pattern displays the dynamic electrical depolarization of the heart over time as corresponding colors. Accordingly, an origin O of an ECG beat may be determined.

As shown in FIG. 8C, a potential area of conduction delay or branch blockage may appear on the cardiac activation map as an area that exhibits a more rapid color change as compared to adjacent areas of the heart. For example, as shown in FIG. 8C, a rapid color change in area 80 indicates a slowdown or blockage in cardiac signal conduction, which may be consistent with a BBB in the His Purkinje conduction system, and in particular, a LBBB. Accordingly, the cardiac activation map may be utilized to identify the location of conduction problems, such as LBBB. In addition, RBBB locations may also be identified, but in general, a RBBB is not considered as clinically significant as a LBBB with respect to CRT.

Improved CRT Pacing

Figure 9A:
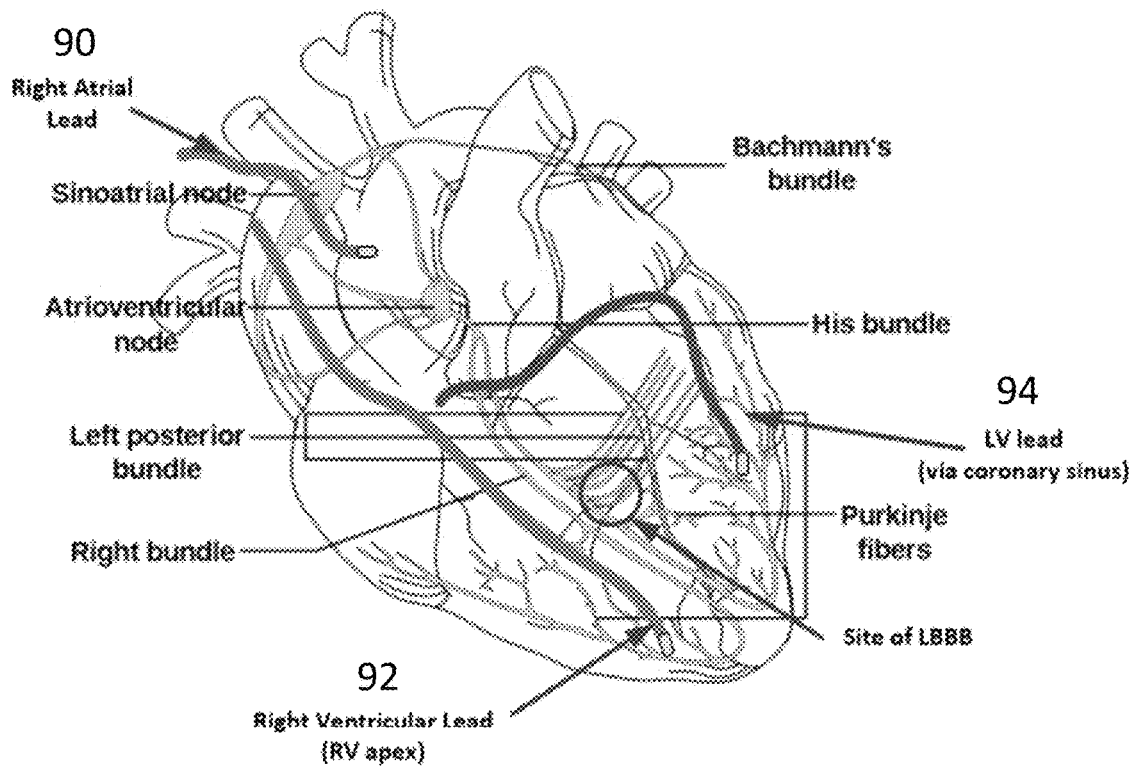
FIGS. 9A and 9B are schematic cardiac views showing pacemaker lead locations that may be utilized for CRT in a patient having LBBB, according to various embodiments of the present disclosure.
Figure 9B:
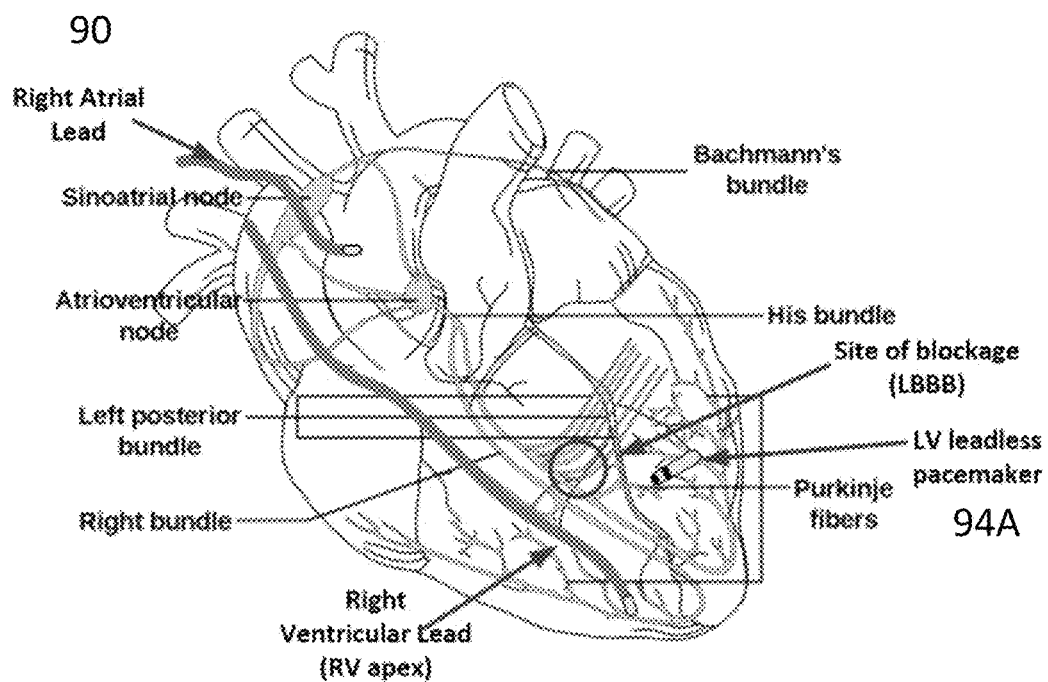

FIGS. 9A and 9B are schematic cardiac views showing pacing lead locations that may be utilized for CRT in a patient having LBBB according to various embodiments of the present disclosure. Referring to FIGS. 9A and 9B, the method may include generating a cardiac activation map as shown in FIGS. 8B and 8C. Based on the electrical conduction sequence shown in the activation map, the method may include positioning CRT electrodes.

In particular, the cardiac activation map may be used to identify the location of the first activation and/or the location of the LBBB. Based on the cardiac activation map, an RA lead 90, a RV lead 92, and/or an LV lead 94 may be positioned with respect to the heart. The RA lead 90 may include a sensing electrode and/or a stimulation electrode disposed in the RA. The RV lead 92 may be positioned at the apex of the RV. The LV lead 94 may be positioned via the coronary sinus and the great cardiac vein or the middle cardiac vein, in a location downstream (e.g., distal) to the LBBB with respect to the direction of electrical conduction through the LV. This location should activate the Purkinje fibers for improved synchronization. In other embodiments, the LV lead 94 may be implanted epicardially on the left ventricle (LV).

As shown in FIG. 9B, the LV lead 94 may be in the form of a leadless pace maker 94A, in some embodiments. The leadless pacemaker 94A can wirelessly communicate to receive the signal for the left ventricular pulse (with adjustable delay) from a primary pacemaker system. FIGS. 9A and 9B exemplify CRT pacing with the implanted RV lead 94 or leadless micro-pacemaker 94A located in the LV.

During CRT pacing, the RA lead 90 would sense/pace the RA. The RV lead 92 may stimulate at the apex of the RV and the LV lead 94 may pace the LV downstream of the LBBB to activate the Purkinje fibers that would otherwise experience a conduction delay due to the LBBB.

Figure 10A:
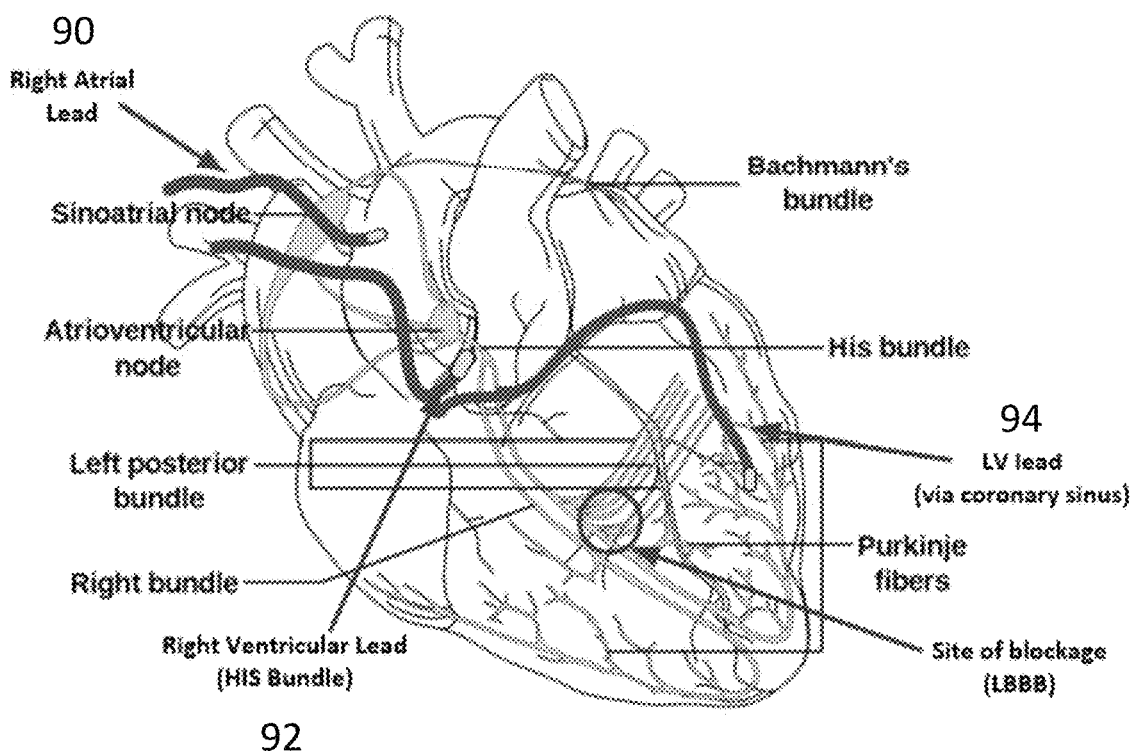
FIGS. 10A and 10B are schematic cardiac views showing pacemaker lead locations that may be utilized for CRT in a patient having LBBB according to various embodiments of the present disclosure.
Figure 10B:
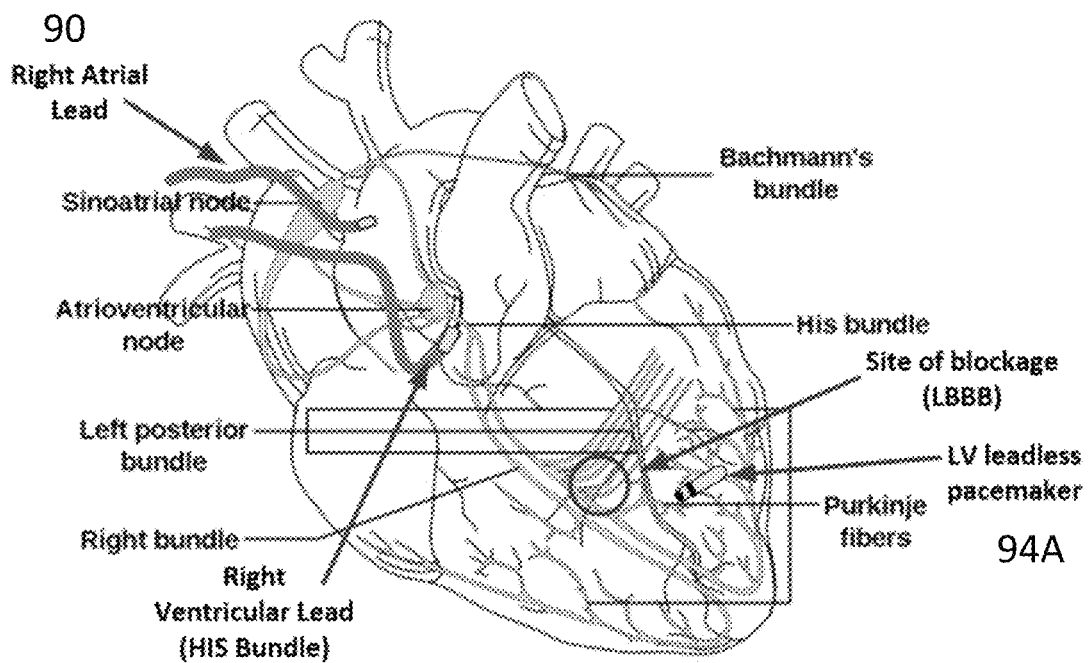

FIGS. 10A and 10B are schematic cardiac views showing lead locations that may be utilized for CRT in a patient having LBBB according to various embodiments of the present disclosure. The method may be similar to the method illustrated in FIGS. 9A and 9B, so only the differences therebetween will be discussed in detail.

Referring to FIGS. 10A and 10B, based on a cardiac activation map, the RV lead 92 may be positioned in a location selected for stimulating at the His bundle. The RA lead 90 may be disposed in the RA and may be configured to detect the presence or absence of the natural heartbeat.

The LV lead 94 may be inserted via the coronary sinus and the great cardiac vein or the middle cardiac vein in a location downstream (e.g., distal) to the LBBB with respect to the direction of electrical conduction through the LV. As shown in FIG. 10B, the LV lead 94 may be in the form of a leadless pacemaker 94A in some embodiments.

During CRT pacing, the RA lead 90 may sense/pace the RA. The RV lead 92 may stimulate at the HIS bundle, and the LV lead may pace the LV downstream of the LBBB to activate the Purkinje fibers that would otherwise experience a conduction delay due to the LBBB.

In various embodiments, the pacing time of the RV lead 92 and the LV lead 94 may be adjustable and may be set according to the distance therebetween and/or the locations thereof. For example, the pacing time of the LV lead 94 may be set to occur at approximately the same time as the depolarization wave reaches the LBBB. In some embodiments, the pacing time of the LV lead 94 may be set to occur after the pacing time of the RV lead 92 and/or the RA lead 90.

Accordingly, each cardiac chamber can be independently detected and paced based on the sequence of activation between the atrium and the ventricle. For dual site ventricular pacing with BBB, a dual electrode site (e.g. HIS bundle and LV distal to the LBBB) can provide the electrical stimulus to the HIS bundle prior to the block and distal from the block with the LV.

Figure 11:
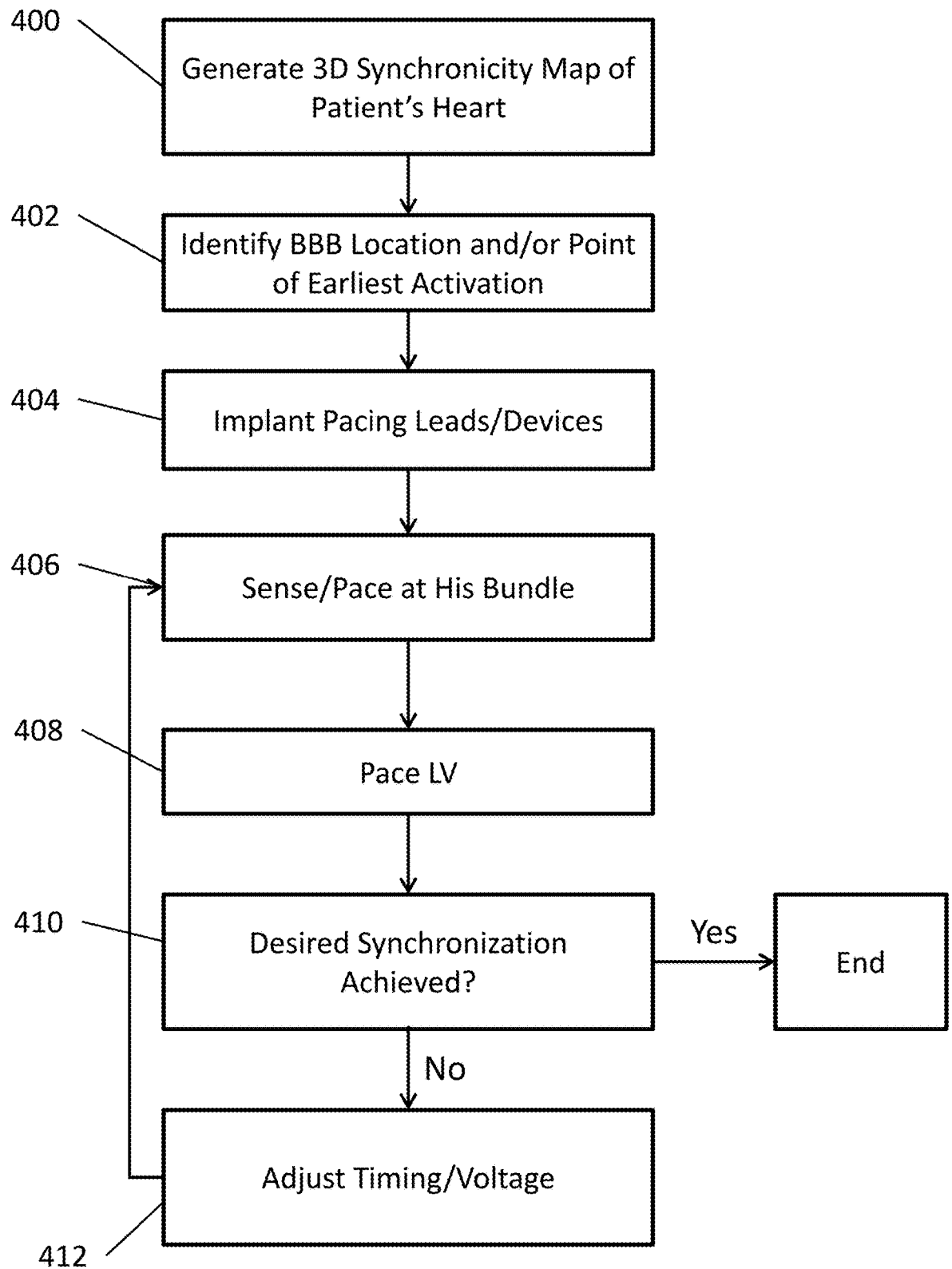
FIG. 11 is a process flow diagram illustrating a method of CRT according to various embodiments of the present disclosure.

FIG. 11 is a process flow diagram illustrating a method of CRT according to various embodiments of the present disclosure. Referring to FIG. 11, in step 400, a 3D cardiac activation map of a patient's heart is generated as discussed above.

In step 402, the activation map may be used to identify a point of earliest activation and/or the location of a conduction blockage. For example, regions of the activation map that show a relatively rapid color change may be detected and used to locate a BBB, in particular LBBB.

In step 404, pacing devices, such as pacing leads and/or micro-pacemakers may be implanted within the heart. However, the method is described with respect to pacing leads. For example, a first pacing device (e.g., an RV lead) may be located at the RV apex or at the His bundle. A second pacing device (e.g., an LV lead) may be located in the LV downstream of a LBBB with respect to the direction of electrical conduction through the LV. A third pacing device (e.g., an RA lead) may be disposed in the RA.

In step 406, the onset of cardiac activation may be detected by detecting the initiation of the intrinsic activation signal, for example, using the RA lead. Once onset has been detected, the RV lead may be used to pace the His bundle. In step 408, after a delay sufficient to allow the depolarization wave to reach the LBBB, the LV lead may be used to pace the LV downstream of the LBBB.

In step 410, a determination may be made as to whether a predetermined amount of cardiac function has been achieved. For example, the cardiac activation map may be updated based on the pacing of the heart and used to determine whether the heart has at least the predetermined amount of function. Determining whether the heart has the desired amount of function may include determining whether the heart has at least predetermined amount of synchronization, activation, or both synchronization and activation. In some embodiments, determining whether the heart has the predetermined amount of function includes determining whether the pacing device has provided a sufficient amount of stimulation to the His bundle, the LV, or both the His bundle and the LV. If the heart has at least the desired amount of function, the method ends.

If the heart does not have the desired amount of function, the delay between the pacing time of the RV (or HIS bundle) and LV leads is adjusted based on the cardiac activation map in step 412. In other embodiments, step 412 may additionally or alternatively include increasing or decreasing a voltage applied by the respective pacing devices. The method then returns to step 406 to detect the onset of cardiac activation.

Figure 12A:
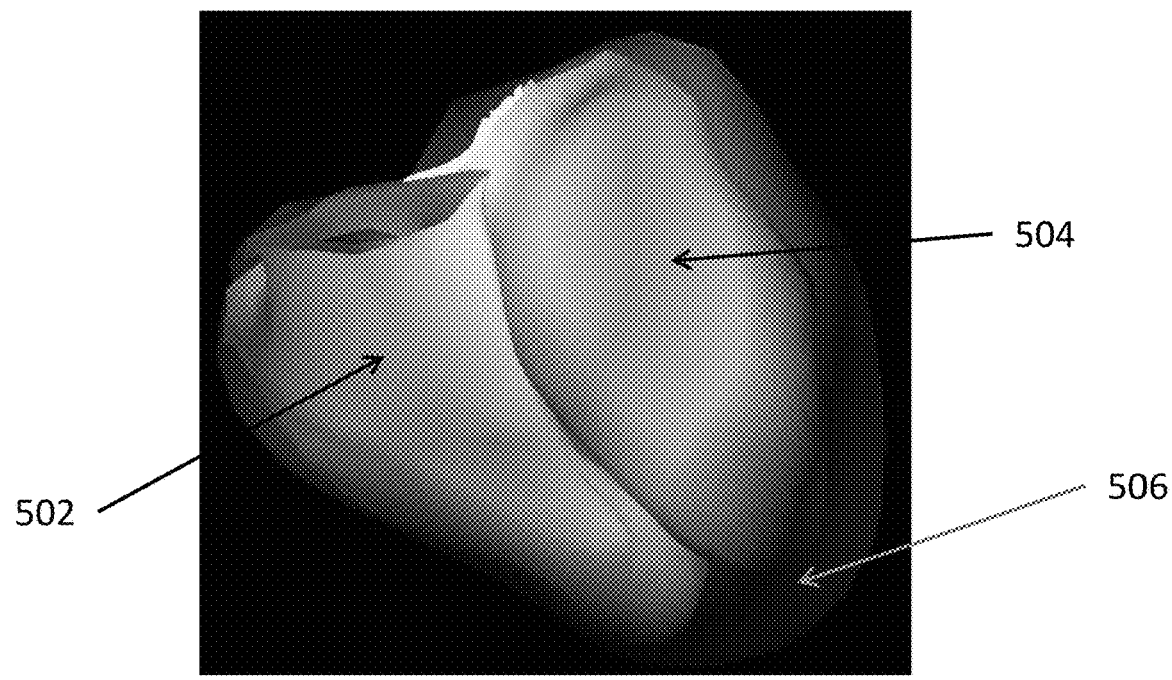
FIGS. 12A and 12B are cardiac activation maps, according to various embodiments of the present disclosure.

FIG. 12A shows a single-beat activation map 500 that may be generated during step 400, according to various embodiments of the present disclosure. Referring to FIGS. 11 and 12A, the activation map 500 may include a 3D heart model that is modified to reflect patient-specific features detected during an MRI or CT scan. For example, the model may include patient-specific cardiac features such as the RV 502, LV 504, myocardium 506, etc.

Figure 12B:
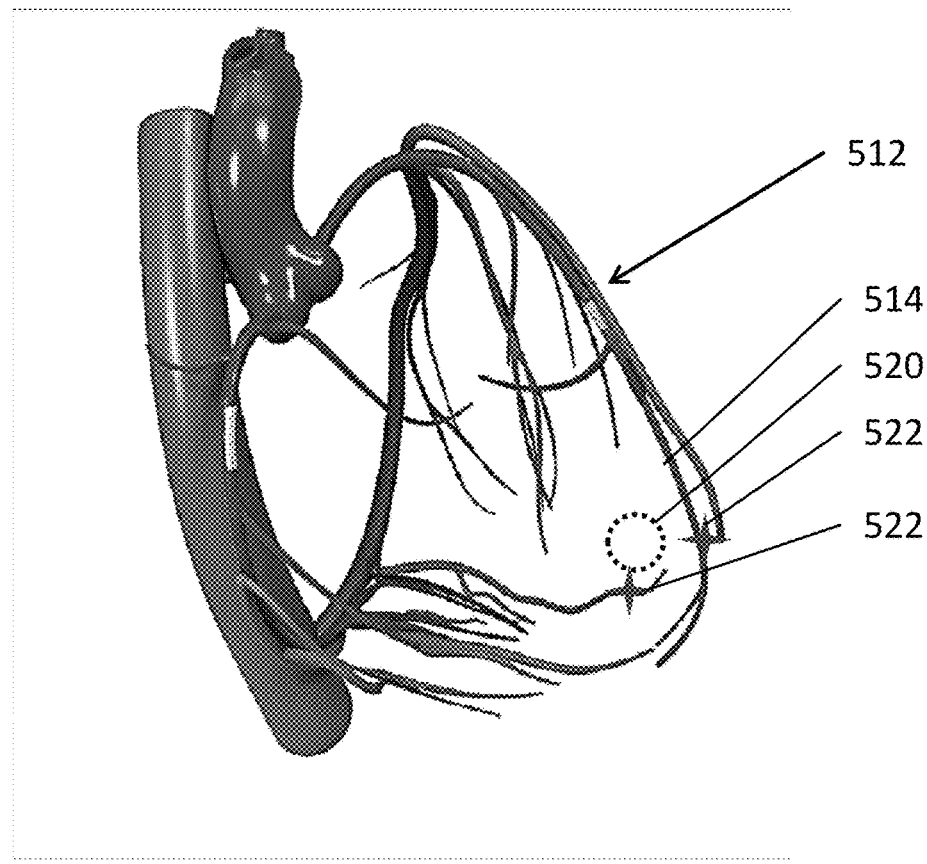

In some embodiments, step 400 may further include modifying the activation map 500 to further display coronary vessel structures 512, as shown in FIG. 12B. Referring to FIGS. 11 and 12B, the activation map 500 may include coronary vessel structures applicable to endocardial lead implantation, such as the left anterior descending artery (LAD) 514. In particular, the coronary vessel structures may be determined based on data from MRI and/or CT images of a patient.

In addition, step 402 may optionally include using the processing unit to identify a suspected BBB location by adding an LBBB marker 520 to the activation map 500. The LBBB marker 520 may identify cardiac tissue in which the progression of a depolarization wave has been slowed or disrupted, due to a LBBB. For example, the LBBB marker 520 may include cardiac tissue downstream of a LBBB that exhibits a conduction delay relative to an expected rate of conduction and/or asynchronous contraction relative to adjacent tissue. In addition, step 402 may optionally include adding a virtual stimulation point 522 to the activation map 500. In particular, the stimulation point 522 may be used to identify a portion of the LAD 514 that is predicted to provide optimal stimulation for restoring synchronicity lost due to the LBBB identified by the LBBB marker 520. For example, the virtual stimulation point 522 may be located in the LAD 514, downstream of the LBBB marker 520 with respect to a direction of electrical conduction through the heart, and as close as possible to the LBBB marker 520.

In other embodiments, step 402 may optionally include providing multiple stimulation points 522 disposed in the same coronary vessel, or in different coronary vessels, at positions downstream from the LBBB marker 520. For example, the stimulation points 522 may be positioned substantially the same distance from the LBBB marker 520 but in different coronary vessels. In other embodiments, the stimulation points 522 may be positioned in different coronary vessels at positions where the corresponding vessels are closest to the LBBB marker 520.

Accordingly, the activation map 500 may allow for a clinician to precisely position a stimulation electrode at an optimized location within a corresponding coronary vessel. In particular, by providing an activation map including a heart model having cardiac vascular structure, along with the location of a LBBB, a clinician may be provided with a single image that identifies an optimal endocardial implantation placement location of the LV pacing lead, as well as shows the path of the coronary vessel through which the pacing lead can be threaded to reach the implantation placement location for CRT patients who also have LBBB.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the scope of the claims. Thus, the present invention is not intended to be limited to the aspects and/or embodiments shown herein but is to be accorded the widest scope consistent with the following claims and the principles and novel features disclosed herein.

What is claimed is:

1. A method of cardiac resynchronization therapy (CRT), comprising:
   generating, using a processing unit, a cardiac activation map comprising a three-dimensional (3D) heart model of the heart that shows coronary vessels of a patient and shows the propagation of electrical signals through the 3D heart model;
   determining the location of a left bundle branch block (LBBB) based on the activation map;
   implanting a first pacing device and a second pacing device into the patient;
   stimulating the His bundle of the heart using the first pacing device;
   stimulating the left ventricle (LV) of the heart at a position downstream of the LBBB with respect to a direction of electrical conduction through the LV using the second pacing device after stimulating the His bundle;
   updating the cardiac activation map based on the stimulation provided by the first and second pacing devices; and
   determining whether the heart has at least a predetermined amount of function based on the updated cardiac activation map.

2. The method of claim 1, wherein the implanting the second pacing device comprises guiding the pacing device through the cardiac vessels displayed on the cardiac activation map.

3. The method of claim 1, further comprising:
   displaying a LBBB marker on the cardiac activation map to identify the LBBB; and
   displaying a stimulation point on the cardiac activation map to identify a location in one of the cardiac vessels that corresponds to the position downstream of the LBBB.

4. The method of claim 1, wherein determining whether the heart has at least a predetermined amount of function comprises determining whether the heart has at least a predetermined amount of synchronization, activation, or both synchronization and activation.

5. The method of claim 1, wherein determining whether the heart has at least a predetermined amount of function comprises determining whether the first pacing device has provided a sufficient amount of stimulation to the His bundle, whether the second pacing device has provided a sufficient amount of stimulation to the LV, or both the first and second pacing devices have provided sufficient amounts of stimulation His bundle and the LV, respectively.

6. The method of claim 1, further comprising in response to determining that the heart does not have a predetermined amount of function:
   increasing or decreasing a delay period between the stimulating of the His bundle and the stimulating of the LV; or
   increasing or decreasing a voltage applied by the first pacing device, the second pacing device, or both the first and second pacing devices.

7. The method of claim 1, wherein determining the location of the LBBB comprises using the processor to identify a region of the heart having relatively slower conduction than adjacent regions of the heart.

8. The method of claim 1, wherein the first and second pacing devices are independently selected from a leadless micro-pacemaker or pacemaker electrode lead.

9. The method of claim 1, wherein the method further comprises:
   implanting a third pacing device; and
   detecting the onset of cardiac activation using the third pacing device.

10. The method of claim 9, wherein the method further comprises pacing the right atrium of the heart using the third pacing device.

11. The method of claim 1, wherein the second pacing device is implanted endocardially through the coronary sinus and the great cardiac vein or the middle cardiac vein.

12. The method of claim 1, wherein the second pacing device is implanted epicardially on the left ventricle (LV).

13. A method of cardiac resynchronization therapy (CRT), comprising:
    generating, using a processing unit, a cardiac activation map comprising a three-dimensional (3D) heart model of the heart that shows coronary vessels of a patient and shows propagation of electrical signals through the 3D heart model;
    determining the location of a left bundle branch block (LBBB) based on the cardiac activation map;
    implanting a first pacing device and a second pacing device into the patient;
    stimulating the right ventricle (RV) using the first pacing device; and
    stimulating the left ventricle (LV) of the heart at a position downstream of the LBBB with respect to a direction of electrical conduction through the LV using the second pacing device after stimulating the His bundle;
    updating the cardiac activation map based on the stimulation provided by the first and second pacing devices; and
    determining whether the heart has at least a predetermined amount of function based on the updated cardiac activation map.

14. The method of claim 13, wherein implanting the second pacing device comprises guiding the pacing device through the cardiac vessels displayed on the cardiac activation map.

15. The method of claim 13, further comprising:
    displaying a LBBB marker on the cardiac activation map to identify a location of the LBBB; and
    displaying a stimulation point on the cardiac activation map to identify a location in one of the cardiac vessels that corresponds to the position downstream of the LBBB.

* * * * *